United States Patent
Nguyen et al.

(10) Patent No.: US 10,456,245 B2
(45) Date of Patent: Oct. 29, 2019

(54) SYSTEM AND METHOD FOR APPLYING MATERIAL TO A STENT

(71) Applicant: Edwards Lifesciences Corporation, Irvine, CA (US)

(72) Inventors: Paul P. Nguyen, Torrance, CA (US); Chris McWilliams, La Canada Flintridge, CA (US); Connor Cady, Newbury Park, CA (US); Cody Jeremiah Kratochvil, Trabuco Canyon, CA (US); Dylan Joseph Kratochvil, Trabuco Canyon, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 68 days.

(21) Appl. No.: 15/611,406

(22) Filed: Jun. 1, 2017

(65) Prior Publication Data

US 2017/0325976 A1 Nov. 16, 2017

Related U.S. Application Data

(63) Continuation of application No. PCT/US2017/032970, filed on May 16, 2017.
(Continued)

(51) Int. Cl.
*A61F 2/24* (2006.01)
*A61L 31/10* (2006.01)

(52) U.S. Cl.
CPC ............ *A61F 2/2415* (2013.01); *A61L 31/10* (2013.01); *A61L 2420/02* (2013.01)

(58) Field of Classification Search
CPC ........................................................ A61F 2/82
(Continued)

(56) References Cited

U.S. PATENT DOCUMENTS

| 3,143,742 A | 8/1964 | Cromie |
| 3,320,972 A | 5/1967 | High et al. |

(Continued)

FOREIGN PATENT DOCUMENTS

| EP | 0125393 A1 | 11/1984 |
| EP | 0143246 A2 | 6/1985 |

(Continued)

OTHER PUBLICATIONS

Krakow, "3F Therapeutics, Inc. Announces the First Clinical Implantation of the 3F Enable Aortic Heart Valve.TM., a Patented, Sutureless Implantation, Replacement Heart Valve Intended to Save Valuable Surgery Time and Reduce Time RelatedComplications . . . "Healthcare Sales & Marketing Network News Feed, Jan. 18, 2005, pp. 1-2.

(Continued)

*Primary Examiner* — Dah-Wei D. Yuan
*Assistant Examiner* — Andrew J Bowman
(74) *Attorney, Agent, or Firm* — Hans P. Smith; Thomas C. Richardson

(57) ABSTRACT

Methods for applying polymeric material to a stent are disclosed. A mandrel is coupled to a stent body. The stent body comprises an inner surface defining a cavity and an outer surface opposing the internal surface. The stent body also has a length along an axis defined by the mandrel between a first end of the stent body and a second end of the stent body. An electrospun material is applied to at least a portion of the stent external surface and to at least a portion of the mandrel to form a coating sheet. A portion of the coating sheet extends from at least one of the first end or second end of the stent to the mandrel. One or both of the stent and the mandrel are moved to apply at least some of the portion of the coating sheet onto the internal surface of the stent body.

21 Claims, 19 Drawing Sheets

Related U.S. Application Data

(60) Provisional application No. 62/337,065, filed on May 16, 2016.

(58) Field of Classification Search
USPC .................................................. 623/1.16
See application file for complete search history.

(56) References Cited

U.S. PATENT DOCUMENTS

| | | |
|---|---|---|
| 3,371,352 A | 3/1968 | Siposs et al. |
| 3,409,013 A | 11/1968 | Berry |
| 3,546,710 A | 12/1970 | Shumakov et al. |
| 3,574,865 A | 4/1971 | Hamaker |
| 3,628,535 A | 12/1971 | Ostrowsky et al. |
| 3,657,744 A | 4/1972 | Ersek |
| 3,686,740 A | 8/1972 | Shiley |
| 3,755,823 A | 9/1973 | Hancock |
| 3,839,741 A | 10/1974 | Haller |
| 3,997,923 A | 12/1976 | Possis |
| 4,035,849 A | 7/1977 | Angell et al. |
| 4,078,468 A | 3/1978 | Civitello |
| 4,079,468 A | 3/1978 | Liotta et al. |
| 4,084,268 A | 4/1978 | Ionescu et al. |
| 4,106,129 A | 8/1978 | Carpentier et al. |
| 4,172,295 A | 10/1979 | Batten |
| 4,217,665 A | 8/1980 | Bex et al. |
| 4,218,782 A | 8/1980 | Rygg |
| 4,259,753 A | 4/1981 | Liotta et al. |
| 4,340,091 A | 7/1982 | Skelton et al. |
| 4,343,048 A | 8/1982 | Ross et al. |
| 4,364,126 A | 12/1982 | Rosen et al. |
| 4,388,735 A | 6/1983 | Ionescu et al. |
| 4,441,216 A | 4/1984 | Ionescu et al. |
| 4,451,936 A | 6/1984 | Carpentier et al. |
| 4,470,157 A | 9/1984 | Love |
| 4,490,859 A | 1/1985 | Black et al. |
| 4,501,030 A | 2/1985 | Lane |
| 4,506,394 A | 3/1985 | Bedard |
| 4,535,483 A | 8/1985 | Klawitter et al. |
| 4,605,407 A | 8/1986 | Black et al. |
| 4,626,255 A | 12/1986 | Reichart et al. |
| 4,629,459 A | 12/1986 | Ionescu et al. |
| 4,680,031 A | 7/1987 | Alonso |
| 4,687,483 A | 8/1987 | Fisher et al. |
| 4,702,250 A | 10/1987 | Ovil et al. |
| 4,705,516 A | 11/1987 | Barone et al. |
| 4,725,274 A | 2/1988 | Lane et al. |
| 4,731,074 A | 3/1988 | Rousseau et al. |
| 4,778,461 A | 10/1988 | Pietsch et al. |
| 4,790,843 A | 12/1988 | Carpentier et al. |
| 4,851,000 A | 7/1989 | Gupta |
| 4,865,600 A | 9/1989 | Carpentier et al. |
| 4,888,009 A | 12/1989 | Lederman et al. |
| 4,914,097 A | 4/1990 | Oda et al. |
| 4,960,424 A | 10/1990 | Grooters |
| 4,993,428 A | 2/1991 | Arms |
| 5,010,892 A | 4/1991 | Colvin et al. |
| 5,032,128 A | 7/1991 | Alonso |
| 5,037,434 A | 8/1991 | Lane |
| 5,147,391 A | 9/1992 | Lane |
| 5,163,955 A | 11/1992 | Love et al. |
| 5,258,023 A | 11/1993 | Reger |
| 5,316,016 A | 5/1994 | Adams et al. |
| 5,326,370 A | 7/1994 | Love et al. |
| 5,326,371 A | 7/1994 | Love et al. |
| 5,332,402 A | 7/1994 | Teitelbaum |
| 5,360,444 A | 11/1994 | Kusuhara |
| 5,370,685 A | 12/1994 | Stevens |
| 5,376,112 A | 12/1994 | Duran |
| 5,396,887 A | 3/1995 | Imran |
| 5,397,351 A | 3/1995 | Pavcnik et al. |
| 5,411,522 A | 5/1995 | Trott |
| 5,423,887 A | 6/1995 | Love et al. |
| 5,425,741 A | 6/1995 | Lemp et al. |
| 5,431,676 A | 7/1995 | Dubrul et al. |
| 5,449,384 A | 9/1995 | Johnson |
| 5,449,385 A | 9/1995 | Religa et al. |
| 5,469,868 A | 11/1995 | Reger |
| 5,476,510 A | 12/1995 | Eberhardt et al. |
| 5,488,789 A | 2/1996 | Religa et al. |
| 5,489,297 A | 2/1996 | Duran |
| 5,489,298 A | 2/1996 | Love et al. |
| 5,500,016 A | 3/1996 | Fisher |
| 5,533,515 A | 7/1996 | Coller et al. |
| 5,549,665 A | 8/1996 | Vesely et al. |
| 5,562,729 A | 10/1996 | Purdy et al. |
| 5,571,215 A | 11/1996 | Sterman et al. |
| 5,573,007 A | 11/1996 | Bobo, Sr. |
| 5,578,076 A | 11/1996 | Krueger et al. |
| 5,584,803 A | 12/1996 | Stevens et al. |
| 5,618,307 A | 4/1997 | Donlon et al. |
| 5,626,607 A | 5/1997 | Malecki et al. |
| 5,628,789 A | 5/1997 | Vanney et al. |
| 5,693,090 A | 12/1997 | Unsworth et al. |
| 5,695,503 A | 12/1997 | Krueger et al. |
| 5,713,952 A | 2/1998 | Vanney et al. |
| 5,716,370 A | 2/1998 | Williamson, IV et al. |
| 5,728,064 A | 3/1998 | Burns et al. |
| 5,728,151 A | 3/1998 | Garrison et al. |
| 5,735,894 A | 4/1998 | Krueger et al. |
| 5,752,522 A | 5/1998 | Murphy |
| 5,755,782 A | 5/1998 | Love et al. |
| 5,766,240 A | 6/1998 | Johnson |
| 5,776,187 A | 7/1998 | Krueger et al. |
| 5,776,188 A | 7/1998 | Shepherd et al. |
| 5,800,527 A | 9/1998 | Jansen et al. |
| 5,814,097 A | 9/1998 | Sterman et al. |
| 5,814,098 A | 9/1998 | Hinnenkamp et al. |
| 5,824,064 A | 10/1998 | Taheri |
| 5,824,068 A | 10/1998 | Bugge |
| 5,840,081 A | 11/1998 | Andersen et al. |
| 5,848,969 A | 12/1998 | Panescu et al. |
| 5,855,563 A | 1/1999 | Kaplan et al. |
| 5,855,601 A | 1/1999 | Bessler et al. |
| 5,865,801 A | 2/1999 | Houser |
| 5,891,160 A | 4/1999 | Williamson, IV et al. |
| 5,895,420 A | 4/1999 | Mirsch, II et al. |
| 5,902,308 A | 5/1999 | Murphy |
| 5,908,450 A | 6/1999 | Gross et al. |
| 5,919,147 A | 7/1999 | Jain |
| 5,921,934 A | 7/1999 | Teo |
| 5,921,935 A | 7/1999 | Hickey |
| 5,924,984 A | 7/1999 | Rao |
| 5,928,281 A | 7/1999 | Huynh et al. |
| 5,957,949 A | 9/1999 | Leonhardt et al. |
| 5,972,004 A | 10/1999 | Williamson, IV et al. |
| 5,984,959 A | 11/1999 | Robertson et al. |
| 5,984,973 A | 11/1999 | Girard et al. |
| 6,010,531 A | 1/2000 | Donlon et al. |
| 6,042,607 A | 3/2000 | Williamson, IV et al. |
| 6,059,827 A | 5/2000 | Fenton, Jr. |
| 6,066,160 A | 5/2000 | Colvin et al. |
| 6,074,418 A | 6/2000 | Buchanan et al. |
| 6,081,737 A | 6/2000 | Shah |
| 6,083,179 A | 7/2000 | Oredsson |
| 6,099,475 A | 8/2000 | Seward et al. |
| 6,106,550 A | 8/2000 | Magovern et al. |
| 6,110,200 A | 8/2000 | Hinnenkamp |
| 6,117,091 A | 9/2000 | Young et al. |
| 6,126,007 A | 10/2000 | Kari et al. |
| 6,264,611 B1 | 7/2001 | Ishikawa et al. |
| 6,322,526 B1 | 11/2001 | Rosenman et al. |
| 6,350,282 B1 | 2/2002 | Eberhardt |
| 6,491,624 B1 | 12/2002 | Lotfi |
| 6,773,457 B2 | 8/2004 | Ivancev et al. |
| 7,037,333 B2 | 5/2006 | Myers et al. |
| 7,998,151 B2 | 8/2011 | St. Goar et al. |
| 8,308,798 B2 | 11/2012 | Pintor et al. |
| 8,323,337 B2 | 12/2012 | Gurskis et al. |
| 8,348,998 B2 | 1/2013 | Pintor et al. |
| 2001/0021872 A1 | 9/2001 | Bailey et al. |
| 2001/0039435 A1 | 11/2001 | Roue et al. |
| 2001/0039436 A1 | 11/2001 | Frazier et al. |
| 2001/0041914 A1 | 11/2001 | Frazier et al. |

(56) References Cited

U.S. PATENT DOCUMENTS

| | | |
|---|---|---|
| 2001/0041915 A1 | 11/2001 | Roue et al. |
| 2001/0049492 A1 | 12/2001 | Frazier et al. |
| 2002/0026238 A1 | 2/2002 | Lane et al. |
| 2002/0032481 A1 | 3/2002 | Gabbay |
| 2002/0058995 A1 | 5/2002 | Stevens |
| 2002/0123802 A1 | 9/2002 | Snyders |
| 2002/0138138 A1 | 9/2002 | Yang |
| 2002/0151970 A1 | 10/2002 | Garrison et al. |
| 2002/0188348 A1 | 12/2002 | DiMatteo et al. |
| 2002/0198594 A1 | 12/2002 | Schreck |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0036795 A1 | 2/2003 | Andersen et al. |
| 2003/0040792 A1 | 2/2003 | Gabbay |
| 2003/0055495 A1 | 3/2003 | Pease et al. |
| 2003/0105519 A1 | 6/2003 | Fasol et al. |
| 2003/0109924 A1 | 6/2003 | Cribier |
| 2003/0114913 A1 | 6/2003 | Spenser et al. |
| 2003/0130729 A1 | 7/2003 | Paniagua et al. |
| 2003/0149478 A1 | 8/2003 | Figulla et al. |
| 2003/0167089 A1 | 9/2003 | Lane |
| 2003/0236568 A1 | 12/2003 | Hojeibane et al. |
| 2004/0019374 A1 | 1/2004 | Hojeibane et al. |
| 2004/0034411 A1 | 2/2004 | Quijano et al. |
| 2004/0044406 A1 | 3/2004 | Woolfson et al. |
| 2004/0106976 A1 | 6/2004 | Bailey et al. |
| 2004/0122514 A1 | 6/2004 | Fogarty et al. |
| 2004/0122516 A1 | 6/2004 | Fogarty et al. |
| 2004/0167573 A1 | 8/2004 | Williamson et al. |
| 2004/0186563 A1 | 9/2004 | Lobbi |
| 2004/0186565 A1 | 9/2004 | Schreck |
| 2004/0193261 A1 | 9/2004 | Berreklouw |
| 2004/0206363 A1 | 10/2004 | McCarthy et al. |
| 2004/0210304 A1 | 10/2004 | Seguin et al. |
| 2004/0210305 A1 | 10/2004 | Shu et al. |
| 2004/0210307 A1 | 10/2004 | Khairkhahan |
| 2004/0225355 A1 | 11/2004 | Stevens |
| 2004/0236411 A1 | 11/2004 | Sarac et al. |
| 2004/0260389 A1 | 12/2004 | Case et al. |
| 2004/0260390 A1 | 12/2004 | Sarac et al. |
| 2005/0010285 A1 | 1/2005 | Lambrecht et al. |
| 2005/0027348 A1 | 2/2005 | Case et al. |
| 2005/0033398 A1 | 2/2005 | Seguin |
| 2005/0043760 A1 | 2/2005 | Fogarty et al. |
| 2005/0043790 A1 | 2/2005 | Seguin |
| 2005/0060029 A1 | 3/2005 | Le et al. |
| 2005/0065594 A1 | 3/2005 | DiMatteo et al. |
| 2005/0065614 A1 | 3/2005 | Stinson |
| 2005/0075584 A1 | 4/2005 | Cali |
| 2005/0075713 A1 | 4/2005 | Biancucci et al. |
| 2005/0075717 A1 | 4/2005 | Nguyen et al. |
| 2005/0075718 A1 | 4/2005 | Nguyen et al. |
| 2005/0075719 A1 | 4/2005 | Bergheim |
| 2005/0075720 A1 | 4/2005 | Nguyen et al. |
| 2005/0075724 A1 | 4/2005 | Svanidze et al. |
| 2005/0080454 A1 | 4/2005 | Drews et al. |
| 2005/0096738 A1 | 5/2005 | Cali et al. |
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137694 A1 | 6/2005 | Haug et al. |
| 2005/0137695 A1 | 6/2005 | Salahieh et al. |
| 2005/0137702 A1 | 6/2005 | Haug et al. |
| 2005/0159811 A1 | 7/2005 | Lane |
| 2005/0165477 A1 | 7/2005 | Anduiza et al. |
| 2005/0165479 A1 | 7/2005 | Drews et al. |
| 2005/0182483 A1 | 8/2005 | Osborne et al. |
| 2005/0182486 A1 | 8/2005 | Gabbay |
| 2005/0192665 A1 | 9/2005 | Spenser et al. |
| 2005/0203616 A1 | 9/2005 | Cribier |
| 2005/0203617 A1 | 9/2005 | Forster et al. |
| 2005/0203618 A1 | 9/2005 | Sharkawy et al. |
| 2005/0216079 A1 | 9/2005 | MaCoviak |
| 2005/0222674 A1 | 10/2005 | Paine |
| 2005/0234546 A1 | 10/2005 | Nugent et al. |
| 2005/0240259 A1 | 10/2005 | Sisken et al. |
| 2005/0251252 A1 | 11/2005 | Stobie |
| 2005/0261765 A1 | 11/2005 | Liddicoat |
| 2005/0283231 A1 | 12/2005 | Haug et al. |
| 2006/0025857 A1 | 2/2006 | Bergheim et al. |
| 2006/0052867 A1 | 3/2006 | Revuelta et al. |
| 2006/0058871 A1 | 3/2006 | Zakay et al. |
| 2006/0058872 A1 | 3/2006 | Salahieh et al. |
| 2006/0074484 A1 | 4/2006 | Huber |
| 2006/0085060 A1 | 4/2006 | Campbell |
| 2006/0095125 A1 | 5/2006 | Chinn et al. |
| 2006/0122634 A1 | 6/2006 | Ino et al. |
| 2006/0122692 A1 | 6/2006 | Gilad et al. |
| 2006/0136054 A1 | 6/2006 | Berg et al. |
| 2006/0149360 A1 | 7/2006 | Schwammenthal et al. |
| 2006/0154230 A1 | 7/2006 | Cunanan et al. |
| 2006/0161249 A1 | 7/2006 | Realyvasquez et al. |
| 2006/0167543 A1 | 7/2006 | Bailey et al. |
| 2006/0195183 A1 | 8/2006 | Navia et al. |
| 2006/0195184 A1 | 8/2006 | Lane et al. |
| 2006/0195185 A1 | 8/2006 | Lane et al. |
| 2006/0195186 A1 | 8/2006 | Drews et al. |
| 2006/0207031 A1 | 9/2006 | Cunanan et al. |
| 2006/0229708 A1 | 10/2006 | Powell et al. |
| 2006/0235508 A1 | 10/2006 | Lane et al. |
| 2006/0241745 A1 | 10/2006 | Solem |
| 2006/0246888 A1 | 11/2006 | Bender et al. |
| 2006/0253191 A1 | 11/2006 | Salahieh et al. |
| 2006/0259134 A1 | 11/2006 | Schwammenthal et al. |
| 2006/0259135 A1 | 11/2006 | Navia et al. |
| 2006/0259136 A1 | 11/2006 | Nguyen et al. |
| 2006/0265056 A1 | 11/2006 | Nguyen et al. |
| 2006/0271172 A1 | 11/2006 | Tehrani |
| 2006/0271175 A1 | 11/2006 | Woolfson et al. |
| 2006/0287717 A1 | 12/2006 | Rowe et al. |
| 2006/0287719 A1 | 12/2006 | Rowe et al. |
| 2006/0293745 A1 | 12/2006 | Carpentier et al. |
| 2007/0005129 A1 | 1/2007 | Damm et al. |
| 2007/0010876 A1 | 1/2007 | Salahieh et al. |
| 2007/0010877 A1 | 1/2007 | Salahieh et al. |
| 2007/0016285 A1 | 1/2007 | Lane et al. |
| 2007/0016286 A1 | 1/2007 | Herrmann et al. |
| 2007/0016288 A1 | 1/2007 | Gurskis et al. |
| 2007/0043435 A1 | 2/2007 | Seguin et al. |
| 2007/0078509 A1 | 4/2007 | Lotfy |
| 2007/0078510 A1 | 4/2007 | Ryan |
| 2007/0100440 A1 | 5/2007 | Figulla et al. |
| 2007/0129794 A1 | 6/2007 | Realyvasquez |
| 2007/0142906 A1 | 6/2007 | Figulla et al. |
| 2007/0142907 A1 | 6/2007 | Moaddeb et al. |
| 2007/0150053 A1 | 6/2007 | Gurskis et al. |
| 2007/0156233 A1 | 7/2007 | Kapadia et al. |
| 2007/0162103 A1 | 7/2007 | Case et al. |
| 2007/0162107 A1 | 7/2007 | Haug et al. |
| 2007/0162111 A1 | 7/2007 | Fukamachi et al. |
| 2007/0179604 A1 | 8/2007 | Lane |
| 2007/0185565 A1 | 8/2007 | Schwammenthal et al. |
| 2007/0198097 A1 | 8/2007 | Zegdi |
| 2007/0203575 A1 | 8/2007 | Forster et al. |
| 2007/0203576 A1 | 8/2007 | Lee et al. |
| 2007/0213813 A1 | 9/2007 | Von Segesser et al. |
| 2007/0225801 A1 | 9/2007 | Drews et al. |
| 2007/0233237 A1 | 10/2007 | Krivoruchko |
| 2007/0239266 A1 | 10/2007 | Birdsall |
| 2007/0239269 A1 | 10/2007 | Dolan et al. |
| 2007/0239273 A1 | 10/2007 | Allen |
| 2007/0244546 A1 | 10/2007 | Francis |
| 2007/0244558 A1 | 10/2007 | Machiraju |
| 2007/0255398 A1 | 11/2007 | Yang et al. |
| 2007/0260305 A1 | 11/2007 | Drews et al. |
| 2007/0265701 A1 | 11/2007 | Gurskis et al. |
| 2007/0270944 A1 | 11/2007 | Bergheim et al. |
| 2007/0282436 A1 | 12/2007 | Pinchuk |

(56) References Cited

U.S. PATENT DOCUMENTS

| | | |
|---|---|---|
| 2007/0288089 A1 | 12/2007 | Gurskis et al. |
| 2008/0021546 A1 | 1/2008 | Patz et al. |
| 2008/0033543 A1 | 2/2008 | Gurskis et al. |
| 2008/0065198 A1 | 3/2008 | Quintessenza |
| 2008/0119875 A1 | 5/2008 | Ino et al. |
| 2008/0154356 A1 | 6/2008 | Obermiller et al. |
| 2008/0281411 A1 | 11/2008 | Berreklouw |
| 2008/0319543 A1 | 12/2008 | Lane |
| 2009/0036903 A1 | 2/2009 | Ino et al. |
| 2009/0192599 A1 | 7/2009 | Lane et al. |
| 2009/0192602 A1 | 7/2009 | Kuehn |
| 2009/0192603 A1 | 7/2009 | Ryan |
| 2009/0192604 A1 | 7/2009 | Gloss |
| 2009/0192605 A1 | 7/2009 | Gloss et al. |
| 2009/0192606 A1 | 7/2009 | Gloss et al. |
| 2010/0161036 A1 | 6/2010 | Pintor et al. |
| 2010/0249894 A1 | 9/2010 | Oba et al. |
| 2010/0249908 A1 | 9/2010 | Chau et al. |
| 2010/0331972 A1 | 12/2010 | Pintor et al. |
| 2011/0022165 A1 | 1/2011 | Oba et al. |
| 2011/0040372 A1* | 2/2011 | Hansen ............ A61B 17/12022 623/1.46 |
| 2011/0135806 A1 | 6/2011 | Grewe et al. |
| 2011/0147251 A1 | 6/2011 | Hodshon et al. |
| 2012/0065729 A1 | 3/2012 | Pintor et al. |
| 2012/0141656 A1 | 6/2012 | Orr et al. |
| 2012/0150288 A1 | 6/2012 | Hodshon et al. |
| 2013/0053949 A1 | 2/2013 | Pintor et al. |
| 2013/0116777 A1 | 5/2013 | Pintor et al. |
| 2014/0058194 A1 | 2/2014 | Soletti et al. |
| 2014/0079758 A1 | 3/2014 | Hall et al. |

FOREIGN PATENT DOCUMENTS

| | | |
|---|---|---|
| SU | 1116573 A1 | 7/1985 |
| SU | 1697790 A1 | 12/1991 |
| WO | 9213502 A1 | 8/1992 |
| WO | 9742871 A1 | 11/1997 |
| WO | 2007146261 A2 | 12/2007 |

OTHER PUBLICATIONS

Sadowski, Jerzy; Kapelak, Boguslaw; Bartus, Krzysztof, "Sutureless Heart Valve Implantation—A Case Study," Touch Briefings, 2005, pp. 48-50.

* cited by examiner

PRIOR ART

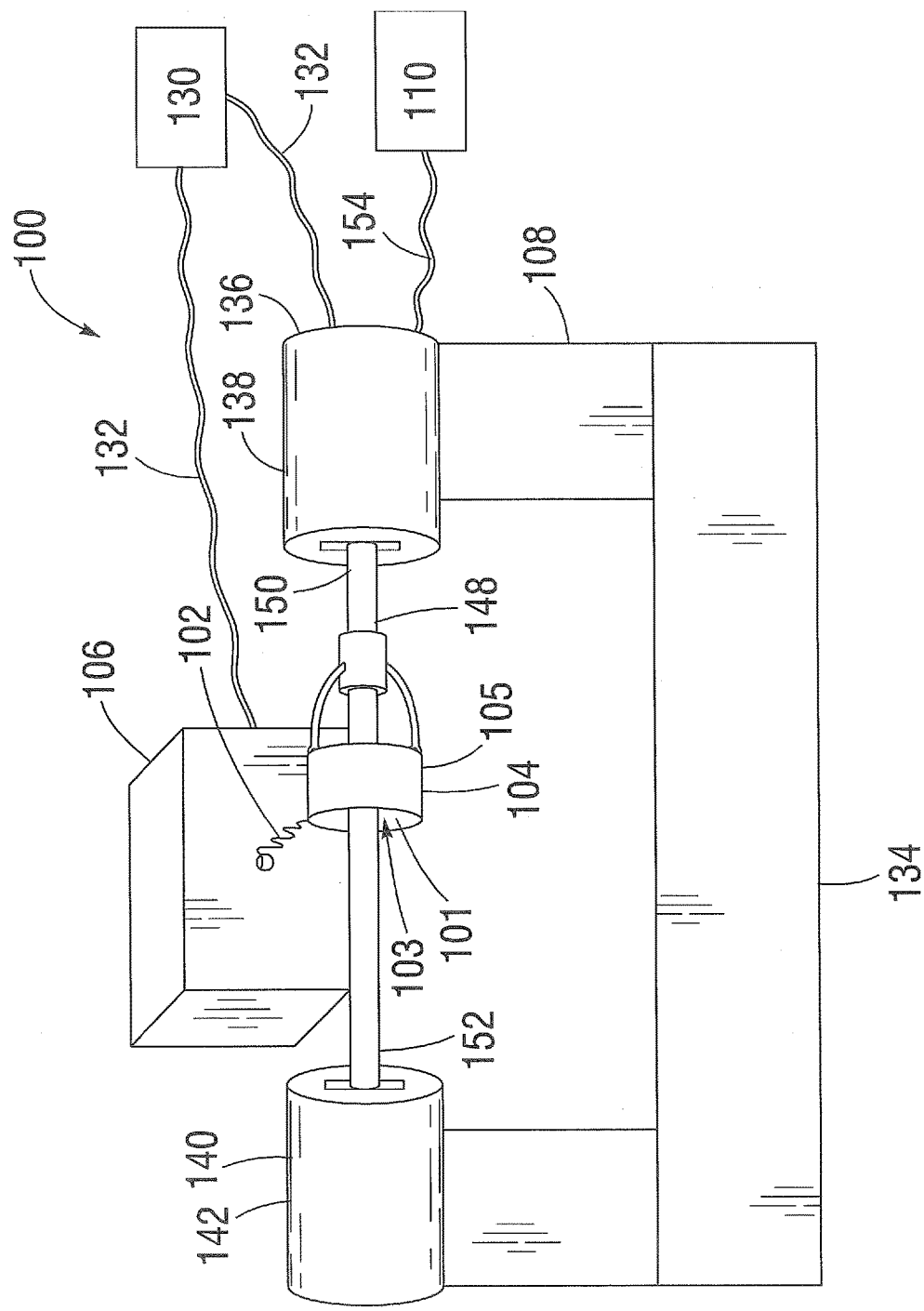

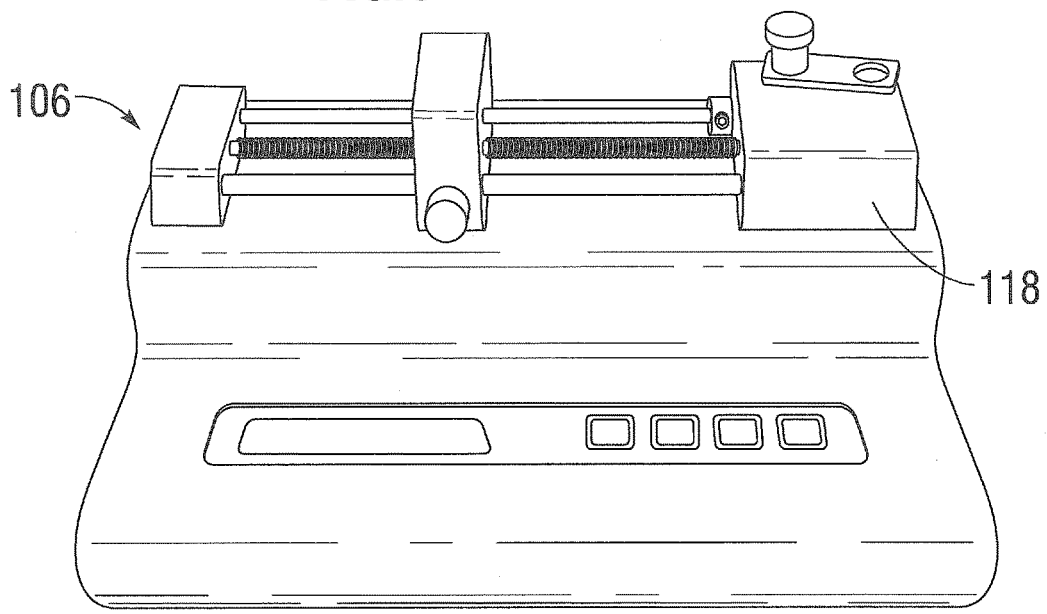
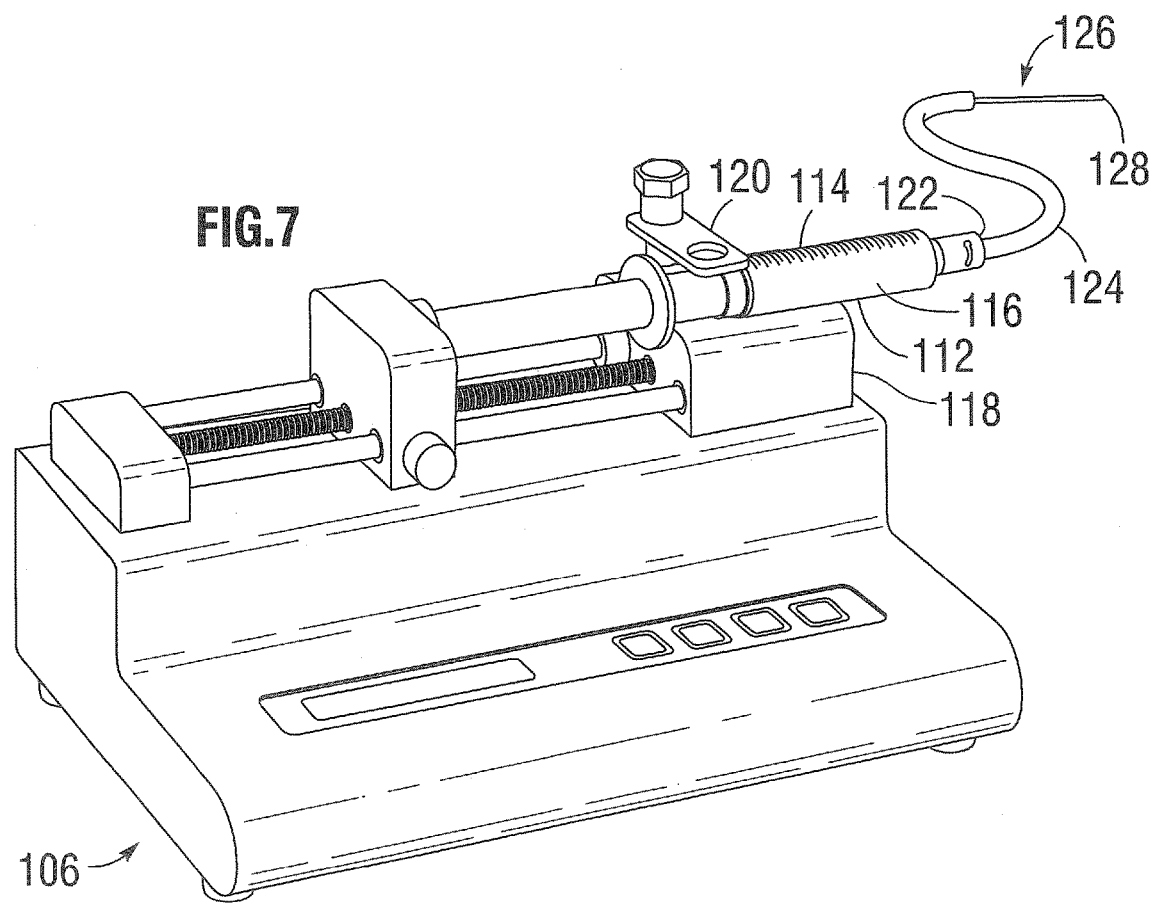

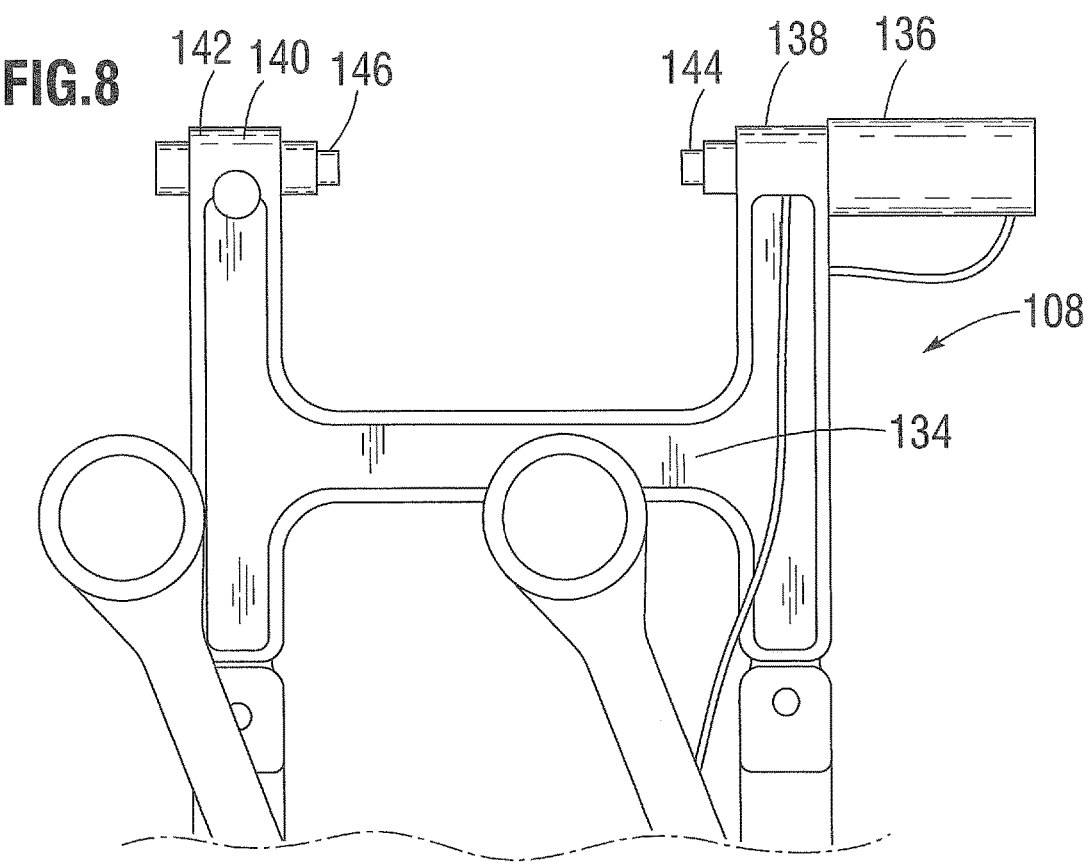
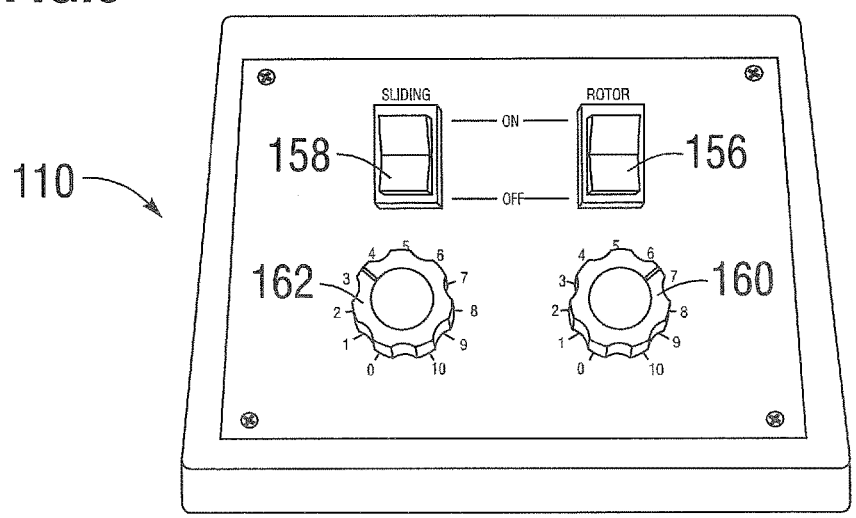

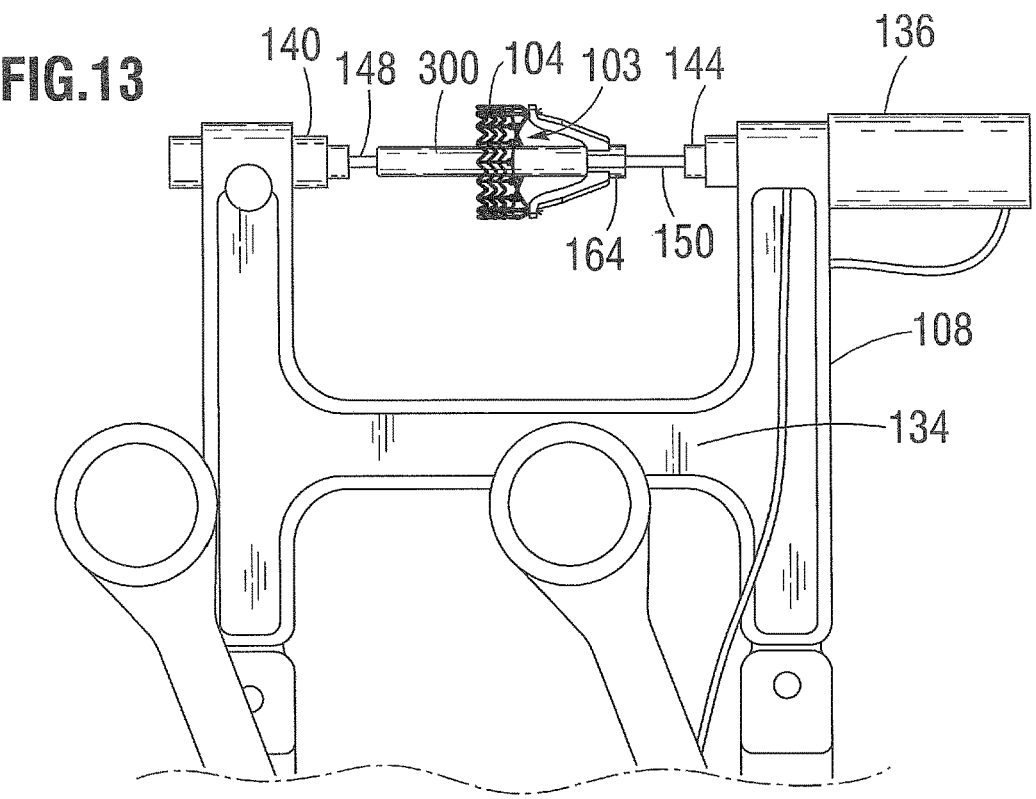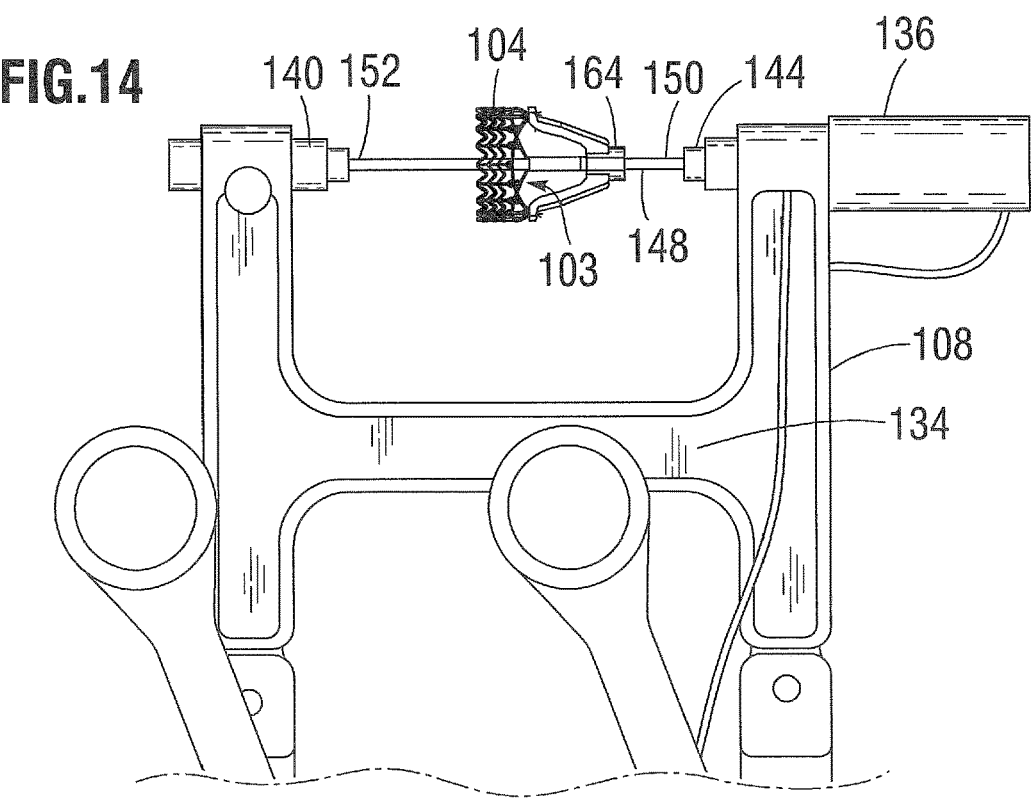

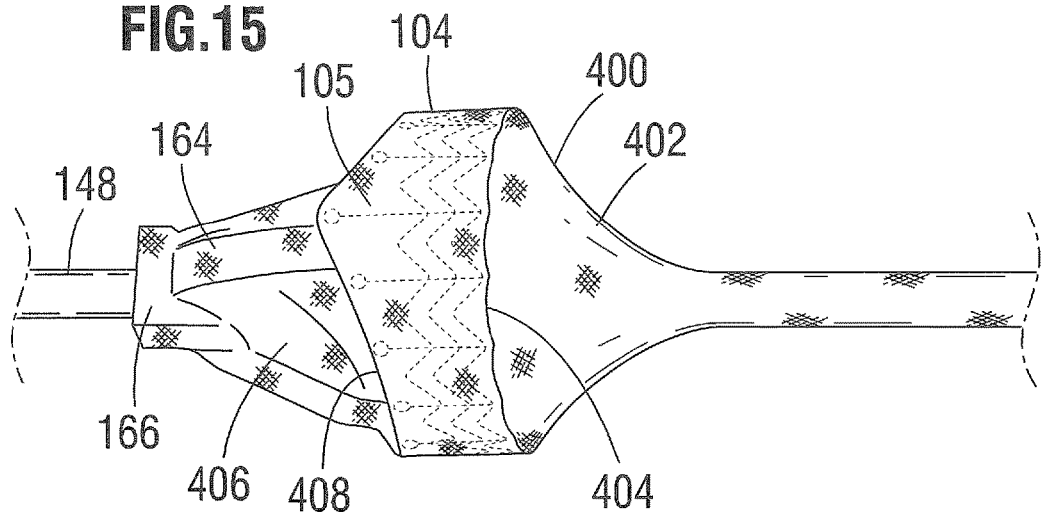
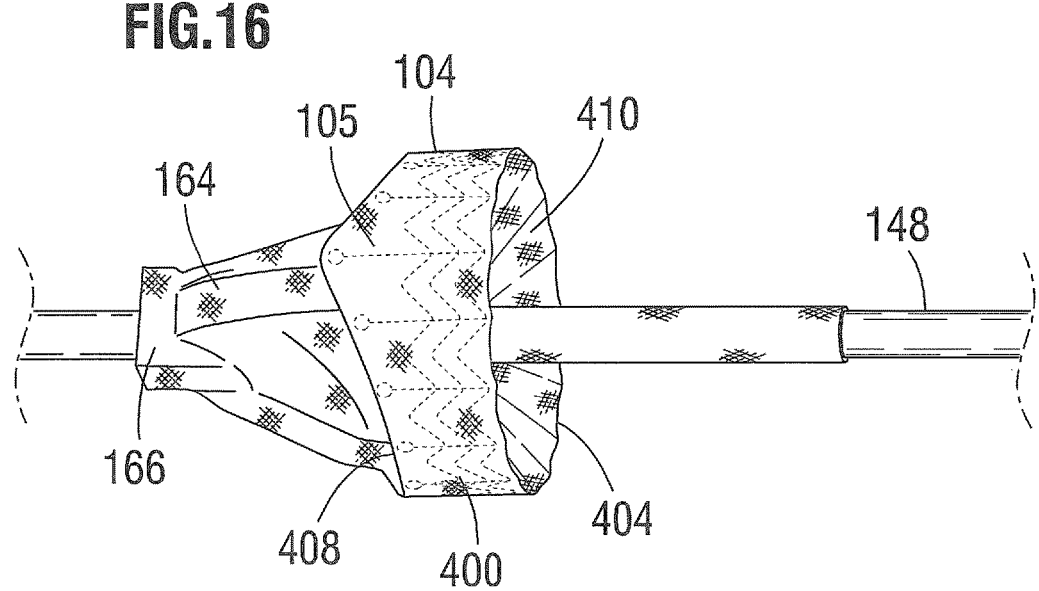

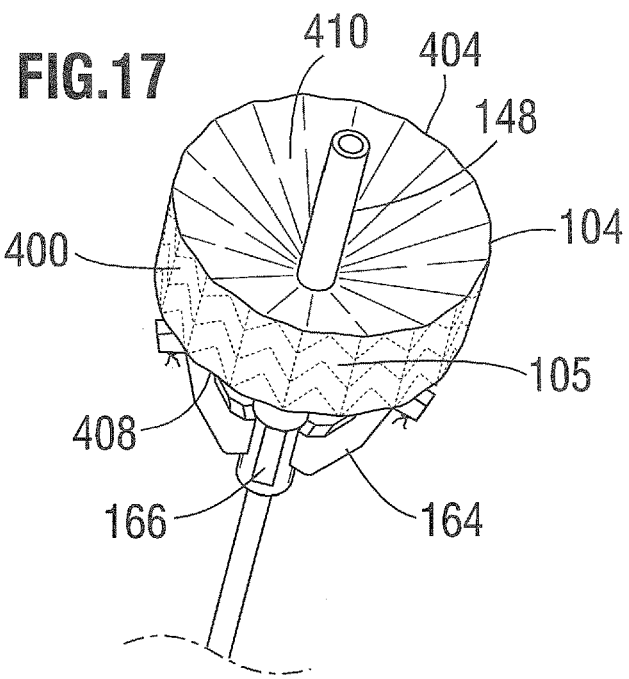
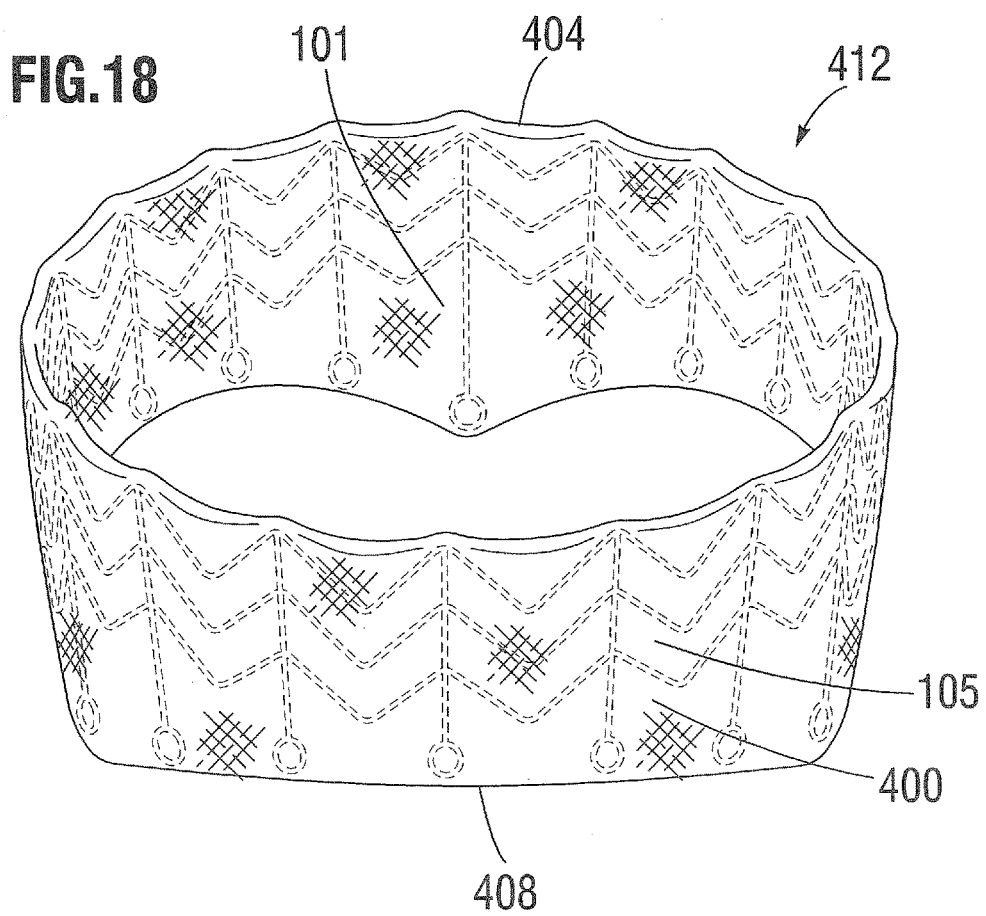

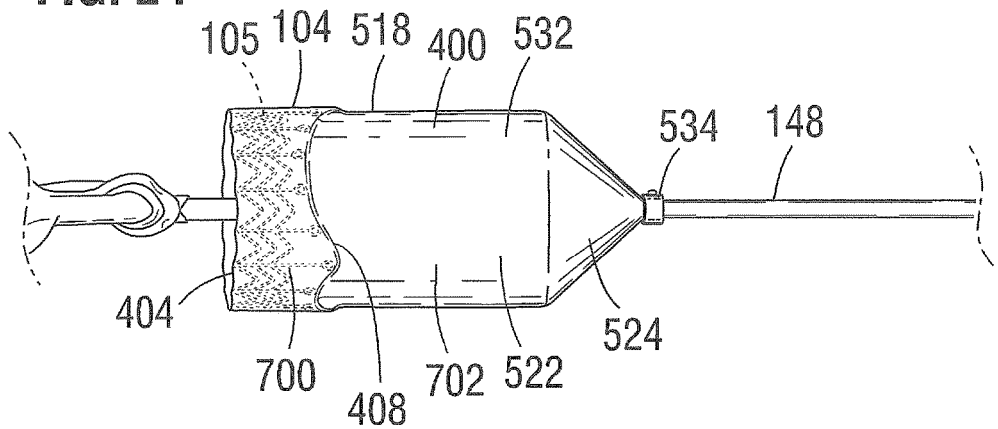
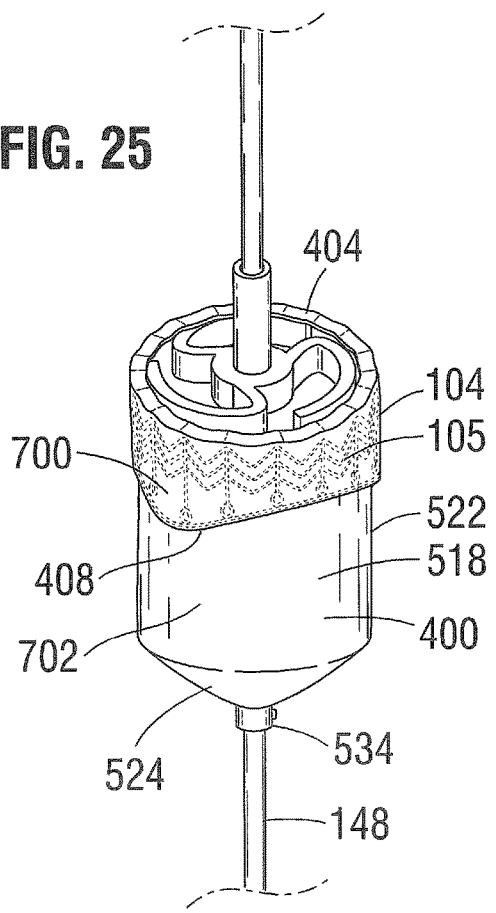
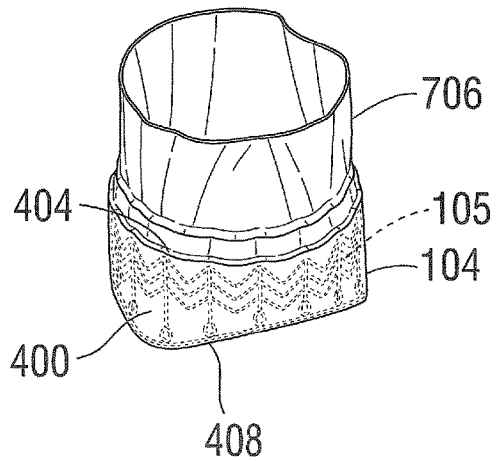

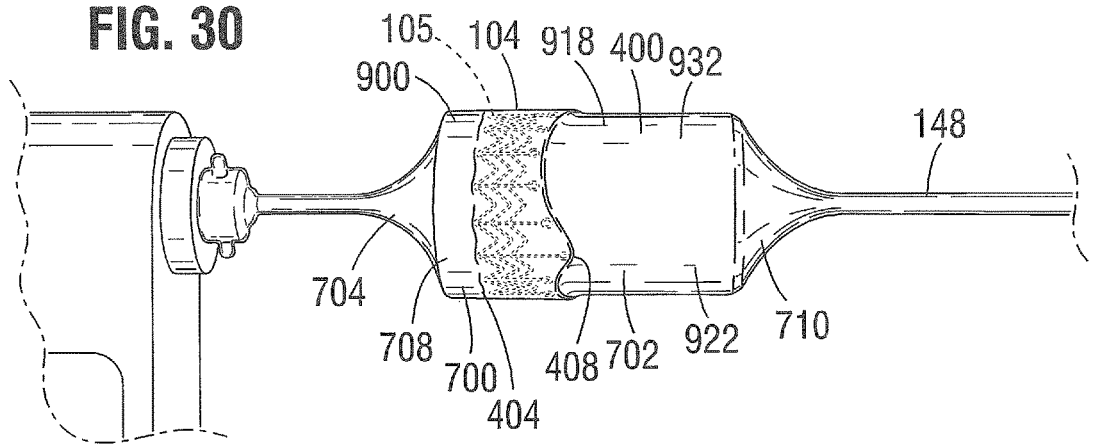
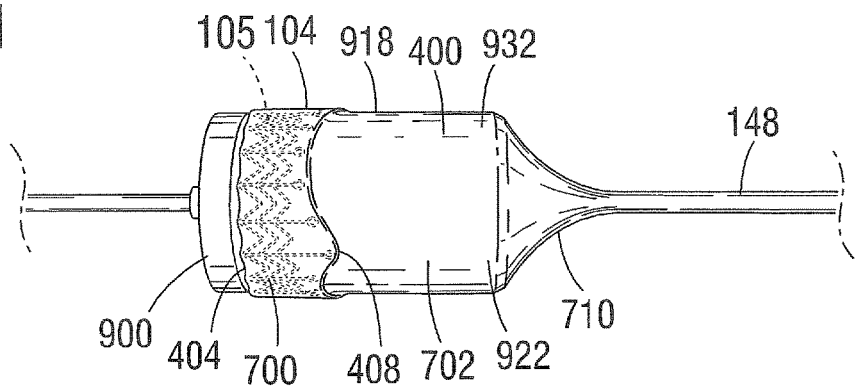
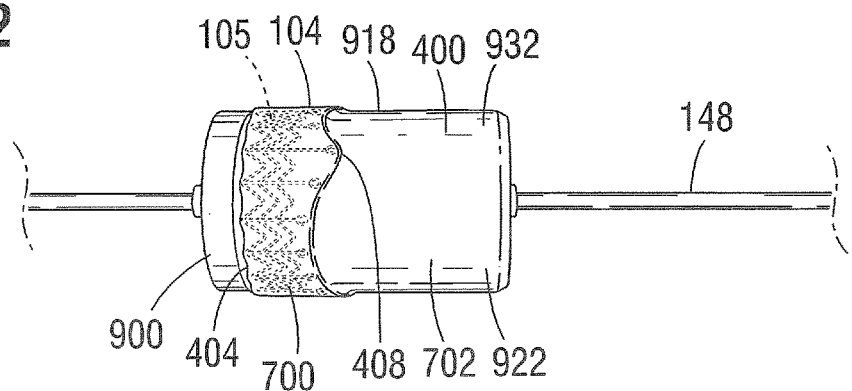

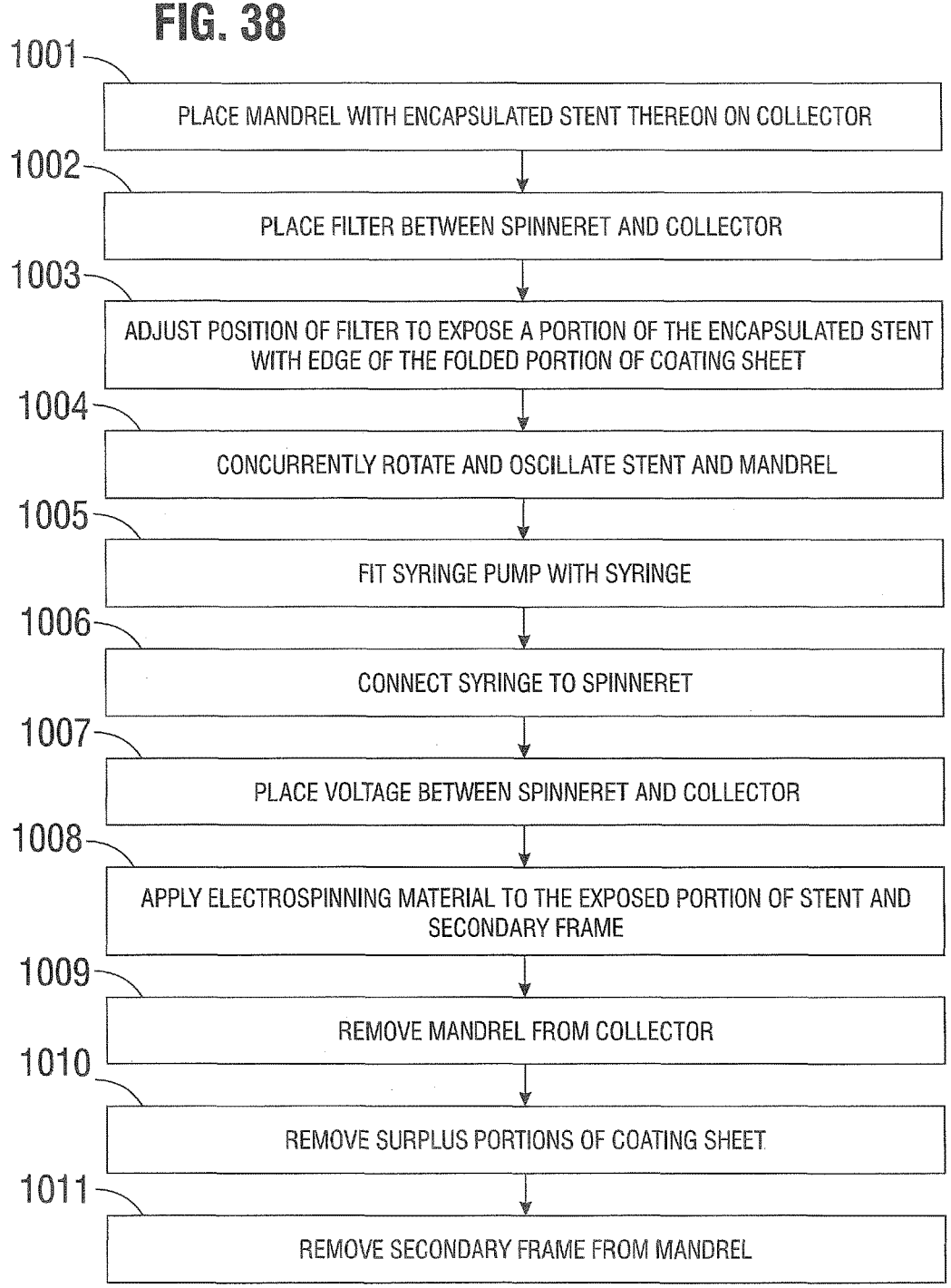

SYSTEM AND METHOD FOR APPLYING MATERIAL TO A STENT

CROSS REFERENCE TO RELATED APPLICATIONS

This application is a continuation of International Application No. PCT/US2017/032970, filed May 16, 2017, which claims the benefit of U.S. Application No. 62/337,065, file May 16, 2016, the entire disclosures which are incorporated by reference.

TECHNICAL FIELD

The disclosed technology relates generally to methods for applying material to a stent, and more particularly, some embodiments relate to methods for applying an electrospun material to inner and outer surfaces of a stent.

DESCRIPTION OF THE RELATED ART

In general, a stent is a conduit configured to be placed in a body to create or maintain a passageway within the body. Varieties of stents exist for different purposes, from expandable coronary, vascular, and biliary stents, to simple plastic stents used to allow urine to flow between a kidney and a bladder.

In the context of a prosthetic heart valve, a stent serves as a structural component that can anchor the prosthetic heart valve to the tissue of a heart valve annulus. Such a stent can have varying shapes or diameters. A stent is typically formed of a biocompatible metal frame, such as stainless steel, cobalt-chrome alloy, or nitinol. In some prosthetic heart-valve applications, the stent is made from laser-cut tubing of a plastically expandable metal, which may subsequently be treated to be self-expanding. Other stents that can be used with a prosthetic heart valve include rigid rings, spirally wound tubes, and other tubes that fit within a heart valve annulus and that define an orifice therethrough for the passage of blood.

Some stents used with prosthetic heart valves are self-expanding, while other stents used with prosthetic heart valves are mechanically expandable, for example, balloon-expandable. A self-expanding stent may be crimped or otherwise compressed into a small tube and may possess sufficient elasticity to spring outward by itself when a restraint such as an outer sheath is removed. In contrast, a balloon-expanding stent may be made of a material that is less elastic and that capable of plastic expansion from the inside out when converting the stent from a contracted diameter to an expanded diameter. The plastic expansion may be accomplished with a balloon or other device, for example, a device with mechanical fingers. With such a balloon-expanding stent, the stent material plastically deforms after the application of a deformation force, such as an inflating balloon or expanding mechanical fingers.

A self-expanding stent or balloon-expanding stent may be used as part of a prosthetic heart valve having a single-stage implantation in which a surgeon secures a hybrid heart valve having an anchoring skirt and valve member to a heart valve annulus as one unit or piece. One solution especially for aortic valve replacement is provided by the Edwards Intuity® valve system available from Edwards Lifesciences of Irvine, Calif. Aspects of the Edwards Intuity valve system are disclosed, for example, in U.S. Pat. No. 8,641,757 to Pintor et al., which is incorporated herein by reference in its entirety. The Edwards Intuity valve is a hybrid of a surgical heart valve and an expandable stent that helps to secure the valve in place. Embodiments of an implantation process use only three sutures, replacing the time-consuming process of placing a dozen or more sutures and tying knots on each. An exemplary delivery system advances the Edwards Intuity valve with the stent at the leading or distal end until it is located within the valve annulus and/or left ventricular outflow tract, at which point a balloon inflates to expand the stent against the aortic annulus and/or ventricular tissue.

FIGS. 1A and 1B show an exemplary hybrid prosthetic heart valve 20 assembled on a valve holder 22 as taught in the prior art, while FIGS. 2A and 2B show the valve holder 22 separated from the heart valve 20. The prosthetic heart valve 20 includes a valve member 24 having an anchoring skirt 26 attached to an inflow end thereof. The valve member 24 is non-collapsible and non-expandable, while the anchoring skirt 26 may expand from the contracted state shown in FIGS. 1A and 1B into an expanded state. The valve member 24 may comprise a surgical valve similar to a Carpentier-Edwards PERIMOUNT Magna® Aortic Heart Valve available from Edwards Lifesciences of Irvine, Calif. The anchoring skirt 26 includes an inner plastically-expandable stent covered with a fabric, for example, a polymeric fabric.

FIGS. 3 and 4 show the assembly of a cloth-covered anchoring skirt 26 as taught in the prior art. The size of the anchoring skirt 26 will vary depending upon the overall size of the heart valve 20. The anchoring skirt 26 comprises an inner stent frame 80, a fabric covering 82, and a band-like lower sealing flange 84. The inner stent frame 80 may comprise a tubular plastically-expandable member having an undulating or scalloped upper end 86 that matches the contours of an inflow portion of the heart valve 20.

In the prior art, the fabric 82 was sewn to the stent frame 80. A tubular section of fabric 82 was drawn taut around the stent frame, inside and out, and sewn thereto to form an intermediate, cloth-covered frame 88. A particular sequence for attaching the tubular section of fabric 82 around the stent frame 80 included providing longitudinal suture markers at 120-degree locations around the fabric to enable registration with similarly circumferentially-spaced commissure features on the stent frame. After surrounding the stent frame 80 with the fabric 82, a series of longitudinal sutures at each of the three 120-degree locations secured the two components together. Furthermore, a series of stitches were provided along the undulating upper end 86 of the stent frame 80 to complete the fabric enclosure.

The polymer cloth attached to the bare metal stent serves to reduce friction between the stent and the body orifice, to secure the prosthetic heart valve in the orifice location, to fill gaps through which fluid could pass through, and to provide a location for tissue in-growth. Applying and sewing the cloth, however, is a time-consuming and laborious process. There is thus a need for an alternative method of applying a fabric or fabric-like material to both the inner and outer surfaces of a stent in a way that reduces labor time and production costs. Embodiments disclosed herein satisfy this need and other needs.

BRIEF SUMMARY OF EMBODIMENTS

According to various embodiments of the disclosed technology, there is disclosed a method that is part of an overall process for applying polymeric material to a stent. This may be accomplished using electrospinning techniques coupled with iterative steps and equipment to cover both the inner surface and the outer surface of a stent.

By way of illustration, electrospun polymeric material may be applied to a metal stent while the stent and a supporting mandrel are rotated by a rotary tool. Over time, the electrospinning process produces a layer of polymeric threads or fibers covering the outside of the metal stent. While the polymeric threads are being applied to the stent, the threads also layer over the mandrel that supports the stent. If the mandrel has a diameter less than the diameter of the stent, then a tapered layer of polymeric material is produced, forming a cone or frustum of polymeric material that extends from the surface of the mandrel to the stent. This cone of polymeric material can then be used as an inner layer of material for the stent by placing the material inside the stent.

The placement of the cone of polymeric material inside the stent may be accomplished by moving the mandrel with respect to the stent, which inverts the cone of polymeric material and wraps it in toward the inner surface of the stent. In this way, both the inner surface and the outer surface of the stent may be fully encased with polymeric material without the need for applying and sewing a pre-made polymeric cloth.

In accordance with a particular embodiment, there is disclosed a method of applying an electrospun material to an inner surface of a stent. The method comprises coupling a mandrel to a stent body. The stent body comprises an inner surface defining a cavity and an outer surface opposing the internal surface. The stent body also has a length along an axis defined by the mandrel between a first end of the stent body and a second end of the stent body. An electrospun material is applied to at least a portion of the stent external surface and to at least a portion of the mandrel to form a coating sheet. A portion of the coating sheet extends from at least one of the first end or second end of the stent to the mandrel. One or both of the stent and the mandrel are moved to apply at least some of the portion of the coating sheet onto the internal surface of the stent body.

In one embodiment, the step of coupling the mandrel to the stent body comprises the steps of attaching the stent body to a valve holder and threading the valve holder onto the mandrel. The step of attaching the stent body to the valve holder comprises the step of suturing the stent body to the valve holder. The stent body comprises a plurality of commissure ends. The valve holder comprises a plurality of stabilizing legs. Each of the plurality of commissure ends is attached to one of the plurality of stabilizing legs. The valve holder may be adhered to the mandrel.

In another embodiment, the mandrel comprises a secondary frame portion. The portion of the coating sheet extends from at least one of the first end or second end of the stent to the secondary frame portion of the mandrel.

A further embodiment comprises the step of attaching the mandrel to a rotary tool and the step of orienting a spinneret so that the spinneret is directed substantially toward the stent body and substantially perpendicular to the axis defined by the mandrel. A voltage is placed between the spinneret and the mandrel. Both the mandrel and the stent body are rotated about the axis defined by the mandrel. Both the mandrel and the stent body are also oscillated along the axis defined by the mandrel.

In a further embodiment, the step of moving one or both of the stent and the mandrel produces an inverted portion of the coating sheet extending inside the cavity of the stent.

In yet a further embodiment, the portion of the coating sheet comprises an excess portion that is not applied onto the inner surface of the stent body. The method further comprises the step of applying at least some of the excess portion onto the outer surface of the stent body.

Each feature, concept, or step is independent, but can be combined with any other feature, concept, or step disclosed in this application.

In accordance with another particular embodiment of the present invention, there is disclosed a method of applying an electrospun material to an inner surface of a stent. The method comprises the step of coupling a mandrel to a stent body. The stent body comprises an inner surface defining a cavity and an outer surface opposing the inner surface. The stent body has a length along an axis defined by the mandrel between a first end of the stent body and a second end of the stent body. A secondary frame is coupled to the mandrel. An electrospun material is applied to at least a portion of the stent outer surface and to at least a portion of the secondary frame to form a coating sheet. A portion of the coating sheet extends from at least one of the first end or second end of the stent to the secondary frame. One or both of the stent and the secondary frame are moved to apply at least some of the portion of the coating sheet onto the inner surface of the stent body.

In one embodiment, the stent has a stent diameter. The secondary frame has a secondary frame diameter. The stent diameter is greater than the secondary frame diameter.

Another embodiment comprises the step of positioning the stent body so that the stent body is between the secondary frame and the valve holder. An alternative embodiment comprises the step of positioning the stent body so that the secondary frame extends within the cavity of the stent body.

In another embodiment, the step of applying the electrospun material further comprises the step of concurrently rotating both the stent body and the secondary frame about the axis defined by the mandrel and oscillating both the stent body and the secondary frame along the axis defined by the mandrel. The step of moving one or both of the stent and the secondary frame produces an inverted portion of the coating sheet extending inside the cavity of the stent.

Each feature, concept, or step is independent, but can be combined with any other feature, concept, or step disclosed in this application.

In accordance with another particular embodiment of the present invention, there is disclosed a method of applying an electrospun material to an inner surface of a stent. The method comprises providing a stent defining an axis and having an inner surface, an outer surface, a first end, a second end, and a central cavity. A mandrel is extended axially within the central cavity of the stent. The stent and the mandrel are rotated along the axis. An electrospun material is applied to at least a portion of the outer surface of the stent, and to at least a portion of the mandrel, while the stent and the mandrel are rotating along or around the axis, so that a sheet of the electrospun material is formed, tapering from at least one of the first end or the second end of the stent to the mandrel. Either or both of the stent and the mandrel are moved along the axis so that at least a portion of the sheet of the electrospun material is inverted within the central cavity of the stent. At least a portion of the inner surface of the stent is covered with the portion of the sheet of the electrospun material.

Each feature, concept, or step is independent, but can be combined with any other feature, concept, or step disclosed in this application.

Other features and aspects of the disclosed technology will become apparent from the following detailed description, taken in conjunction with the accompanying drawings, which illustrate, by way of example, the features in accordance with embodiments of the disclosed technology. The summary is not intended to limit the scope of any inventions described herein, which are defined solely by the claims attached hereto.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and should not be considered limiting of the breadth, scope, or applicability thereof. For clarity and ease of illustration, these drawings are not necessarily made to scale.

FIG. 5 is a diagrammatic view of a system for applying an electrospinning material to a stent in accordance with one embodiment of the technology described herein, the system comprising a syringe pump, a collector, a controller, and a high-voltage power supply.

FIG. 6 is a perspective view of a syringe pump for use in the system of FIG. 5, in accordance with one embodiment of the technology described herein.

FIG. 7 is a perspective view of a syringe pump, syringe, and spinneret for use in the system of FIG. 5, in accordance with one embodiment of the technology described herein.

FIG. 8 is a perspective view of a collector for use in the system of FIG. 5, in accordance with one embodiment of the technology described herein, the collector comprising a base configured to hold a rotary tool at a first end and a rotary holder at a second end.

FIG. 9 is a perspective view of a controller for use in the system of FIG. 5, in accordance with one embodiment of the technology described herein, the controller comprising a rotor switch, a slide switch, a rotor speed dial, and a slide speed dial.

FIG. 13 is a perspective view of a collector for use in the system of FIG. 5, in accordance with one embodiment of the technology described herein, the collector having a mandrel on which a valve holder, a stent, and a machined piece of metal are threaded.

FIG. 14 is a perspective view of a collector for use in the system of FIG. 5, in accordance with one embodiment of the technology described herein, the collector having a mandrel without the machined piece of metal.

FIG. 15 is a side elevational view of a mandrel, valve holder, and stent on which a coating sheet has been formed, in accordance with one embodiment of the technology described herein, the coating sheet having a first cone portion extending from an end of the stent to the mandrel.

FIG. 16 is a side elevational view of a mandrel, valve holder, and stent on which a coating sheet has been formed, in accordance with one embodiment of the technology described herein, the coating sheet having an inverted portion extending from an end of the stent to the mandrel.

FIG. 17 is a perspective view of a mandrel, valve holder, and stent on which a coating sheet has been formed, in accordance with one embodiment of the technology described herein, with the portion of the coating sheet covering the valve holder having been removed.

FIG. 18 is a perspective view of a covered stent in accordance with one embodiment of the technology described herein, the covered stent having a coating sheet applied to both the inner surface and the outer surface of the stent.

FIG. 24 is a side elevational view of a mandrel, a stent, and a secondary frame on which a coating sheet has been formed, in accordance with one embodiment of the technology described herein, with surplus portions of the coating sheet having been removed.

FIG. 25 is a perspective view of a mandrel, a stent, and a secondary frame on which a coating sheet has been formed, in accordance with one embodiment of the technology described herein, with surplus portions of the coating sheet having been removed.

FIG. 26 is a perspective view of a covered stent in accordance with one embodiment of the technology described herein, the covered stent having a coating sheet applied to both the inner surface and the outer surface of the stent with an excess portion extending beyond the end of the stent.

FIG. 30 is a side elevational view of a mandrel, a stent, an auxiliary holder, and a secondary frame on which a coating sheet has been formed, in accordance with one embodiment of the technology described herein.

FIG. 31 is a side elevational view of a mandrel, a stent, an auxiliary holder, and a secondary frame on which a coating sheet has been formed, in accordance with one embodiment of the technology described herein, with surplus portions of the coating sheet on the side of the auxiliary holder having been removed.

FIG. 32 is a side elevational view of a mandrel, a stent, an auxiliary holder, and a secondary frame on which a coating sheet has been formed, in accordance with one embodiment of the technology described herein, with surplus portions of the coating sheet on both sides having been removed.

FIG. 38 is a flow chart showing a method of applying an electrospun material to a stent on an exposed side of a filter, in accordance with one embodiment of the technology described herein.

Figure 1A:
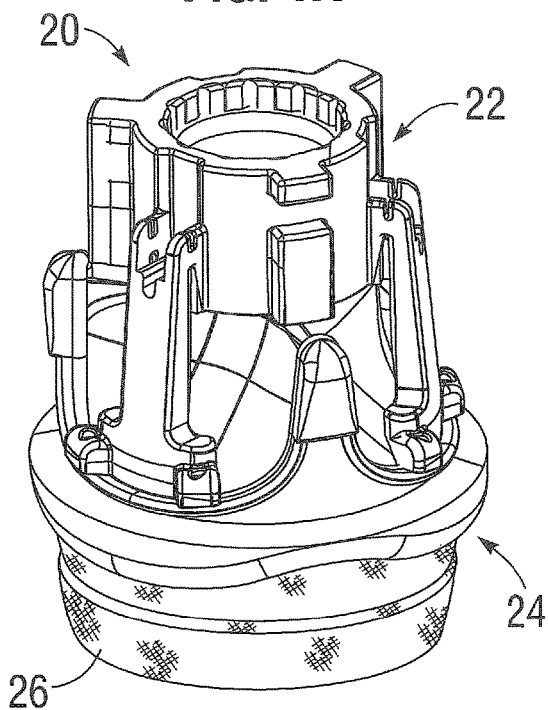
FIGS. 1A and 1B are perspective views of an exemplary hybrid prosthetic heart valve assembled on a valve holder as taught in the prior art.
Figure 1B:
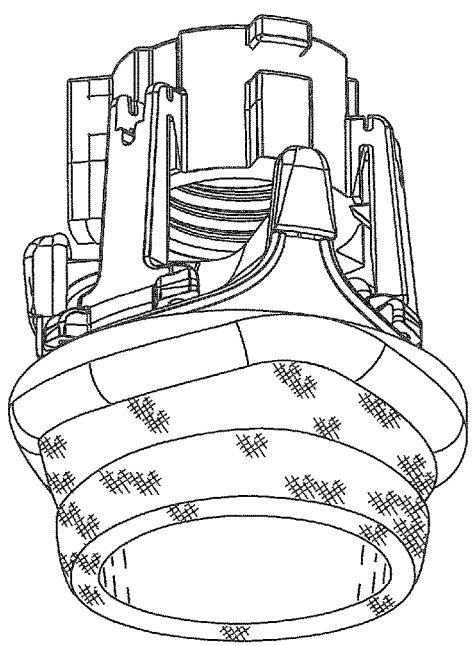
Figure 2A:
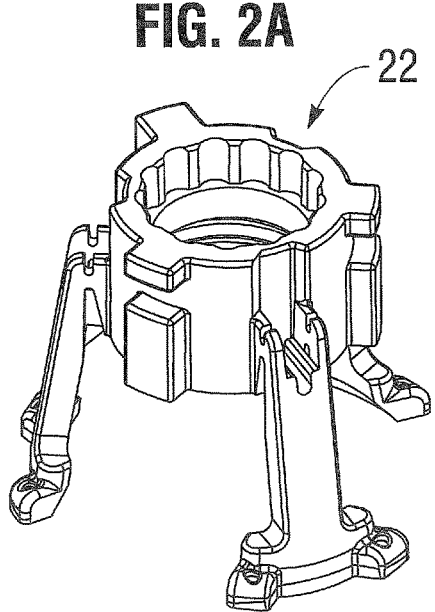
FIGS. 2A and 2B are perspective views of the valve holder of FIGS. 1A and 1B separated from the heart valve.
Figure 2B:
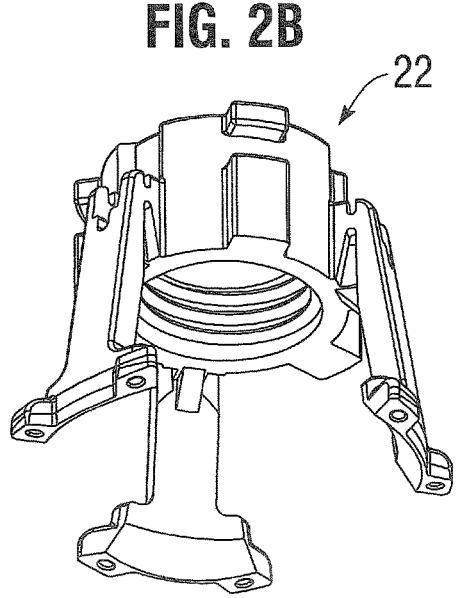

The figures are not intended to be exhaustive or to limit the invention to the precise form disclosed. The invention can be practiced with modification and alteration, and the disclosed technology is limited only by the claims and the equivalents thereof.

DETAILED DESCRIPTION OF THE EMBODIMENTS

Embodiments of the technology disclosed herein are directed toward methods for applying material to a stent. More particularly, various embodiments of the technology disclosed herein relate to methods for applying an electrospun material to the inner and outer surfaces of a stent.

Referring to FIG. 5 of the illustrative drawings, there is shown a system 100 for applying an electrospinning material 102 to a stent 104. The system 100 comprises a source of electrospinning material 106, a collector 108, and a controller 110. The source of electrospinning material is any suitable device, for example, a device comprising a spinneret electrically coupled to a voltage source. As discussed below, embodiments of the source include at least one syringe pump, at least one syringe mounted on the at least one syringe pump, and at least one syringe needle fluidly coupled to the at least one syringe, where the at least one syringe needle is a spinneret. In some embodiments, the voltage source is electrically coupled to the at least one syringe needle. As used herein, the term "syringe pump" may include the combination of a syringe pump, syringe, and syringe needle, as will be apparent by context.

In one embodiment, the electrospinning material 102 is a solution of polyethylene terephthalate (PET). The PET solution may be created by mixing PET, for example, at about 10% to 20% by weight, with a suitable solvent or mixture of solvents, such as hexafluoroisopropanol (HFIP) at about 80% to 90% by weight, and permitting the PET to dissolve fully. In a particular embedment, the PET solution is created by mixing PET at about 15% to 18% by weight with a solvent such as HFIP at about 82% to 85% by weight. Instead of or in addition to PET, another polymer may be used, either alone or in combination, such as a polymer selected from the group consisting of polytetrafluoroethylene (PTFE), polycaprolactone (PCL), polydioxanone (PDO), polyglycolic acid (PGA), and polyurethane (PU). Additionally, one or more drugs and/or biologically active ingredients may be added to the solution. Similarly, other solvents or mixtures thereof are used in other embodiments.

Figure 3:
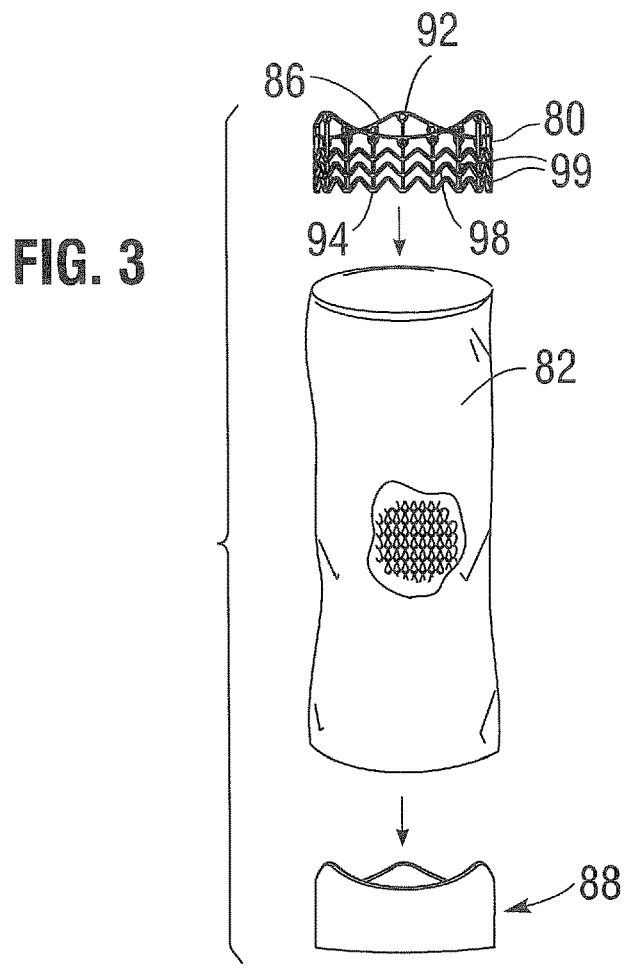
FIG. 3 is an exploded assembly view of a portion of a cloth-covered anchoring skirt for coupling to a surgical heart valve as taught in the prior art.
Figure 4:
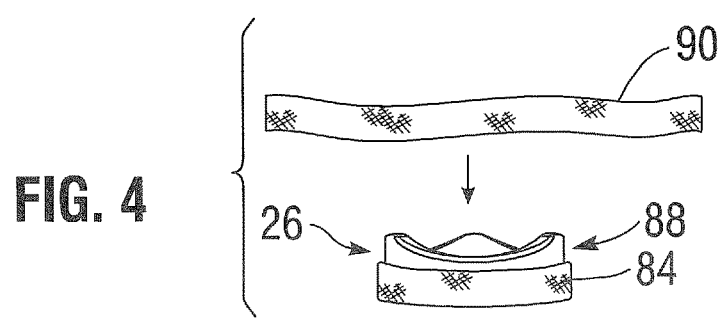
FIG. 4 is an exploded assembly view of the portion of the cloth-covered anchoring skirt shown in FIG. 3 with a lower sealing flange secured thereto as taught in the prior art.

In one embodiment, the stent 104 is a stent for use as part of a prosthetic heart valve, such as the Edwards Intuity® valve system disclosed in U.S. Pat. No. 8,641,757 to Pintor et al. or the Edwards SAPIEN® Transcatheter Heart Valve. The stent 104 may be an expandable stainless-steel stent. The material, however, is not limited to stainless steel, and other materials such as cobalt-chrome alloys and nitinol may be used. A first end 86 of the stent (see FIG. 3) follows a generally circular, undulating path having alternating arcuate troughs and pointed peaks that generally correspond to the undulating contour of the underside of a sewing ring (not shown) for use as part of a prosthetic heart valve. A second end 94 of the stent substantially describes a circle without the undulations. A mid-section of the stent has three rows of expandable struts 98 extending circumferentially in a sawtooth or chevron pattern between axially-extending struts 99. The first end 86 of the stent comprises a continuous, relatively thicker reinforcing ring having a substantially constant diameter interrupted by eyelets 92. The stent frame 80 comprises an inner surface 101 defining a cavity 103 and an outer surface 105 opposing the inner surface.

The syringe pump 106 serves as the source of the electrospinning material 102 to be applied to the stent 104. Some embodiments include a plurality of syringe pumps. In general, electrospinning uses an electrical charge to draw very fine (typically on the micro- or nanometer scale) fibers from a liquid, such as a polymer solution or a polymer melt. In one electrospinning method, the polymer is discharged through a charged orifice toward a target, wherein the orifice and the target have opposing electrical charges. A voltage source is provided that creates a first charge at the charged orifice and an opposing charge at the target. The polymer is electrostatically charged by contact with the charged orifice. The electrostatically charged polymer is then collected at the target. Electrospinning PTFE is described in U.S. Patent Application Publication No. 2010/0193999 A1, which is incorporated herein by reference.

An embodiment of a syringe pump 106 is shown in FIG. 6. In this embodiment, the syringe pump 106 is a KDS100 syringe pump made by KD Scientific Inc. of Holliston, Mass., although other syringe pumps, pressure sources, and/or solution reservoir/dispensers may alternatively be used. In a particular embodiment, the syringe pump 106 is configured for a flow rate of about 5.5 milliliters per hour.

The syringe pump 106 is used with a syringe 112, as shown in FIG. 7. In one embodiment, the syringe 112 is a 10-mL plastic syringe, although other syringes may alternatively be used. The syringe 112 comprises a cylindrical body 114 defining a reservoir 116, into which an amount of the electrospinning material 102 is placed. After the reservoir 116 is filled, the syringe 112 is placed horizontally on the syringe holder block 118 of the syringe pump 106 and is fixed in place using a syringe clamp 120. In other embodiments, the syringe is fixed in another orientation, for example, vertically, or at a different angle.

Once the syringe pump 106 is fitted with a loaded syringe 112, the orifice 122 of the syringe may be connected to a plastic tube that leads to a spinneret 126 having a spinneret tip 128. In one embodiment, the spinneret 126 is a stainless-steel needle having an inner diameter of approximately 0.6 millimeters, although other spinnerets may alternatively be used. The electrospinning material 102 is electrostatically drawn from the spinneret tip 128 by placing or applying a high voltage or potential difference between the spinneret tip and the collector 108 using a high-voltage power supply 130 connected by wires 132 to the spinneret and the collector. In one embodiment, the high-voltage power supply 130 is an about 5 kV to 50 kV direct-current power supply. In a particular embodiment, the high-voltage power supply 130 is configured to apply a voltage of approximately 14 kV. Other potentials are applied in other embodiments, for example, where the electrospinning parameters include one of a polymer other than PET and/or a solvent other than HFIP.

An embodiment of a collector 108 is shown in FIG. 8. The collector 108 comprises a base 134 configured to hold a rotary tool 136 at a first end 138 and a rotary holder 140 at a second end 142. The rotary tool 136 comprises a rotor motor configured to rotate a first collet 144 and a slide motor configured to slide the first collet back and forth with respect to the rotatory holder 140 in an oscillating fashion. The rotary holder 140 has a corresponding second collet 146. A mandrel 148 (see FIG. 5) may be placed in the collector 108 by placing a first end 150 of the mandrel in the first collet 144 and a second end 152 of the mandrel in the second collet 146. The rotary tool 136 is coupled via a cable 154 to the controller 110 for controlling the rotor and slide motors.

An embodiment of a controller 110 is shown in FIG. 9. The controller 110 shown in FIG. 9 includes a DC motor controller comprising a rotor switch 156 for turning the rotor motor on and off, a slide switch 158 for turning the slide motor on and off, a rotor speed dial 160 for controlling the rotational speed of the rotor motor, and a slide speed dial 162 for controlling the oscillation speed of the slide motor. Other types of controllers are used in other embodiments.

Figure 10:
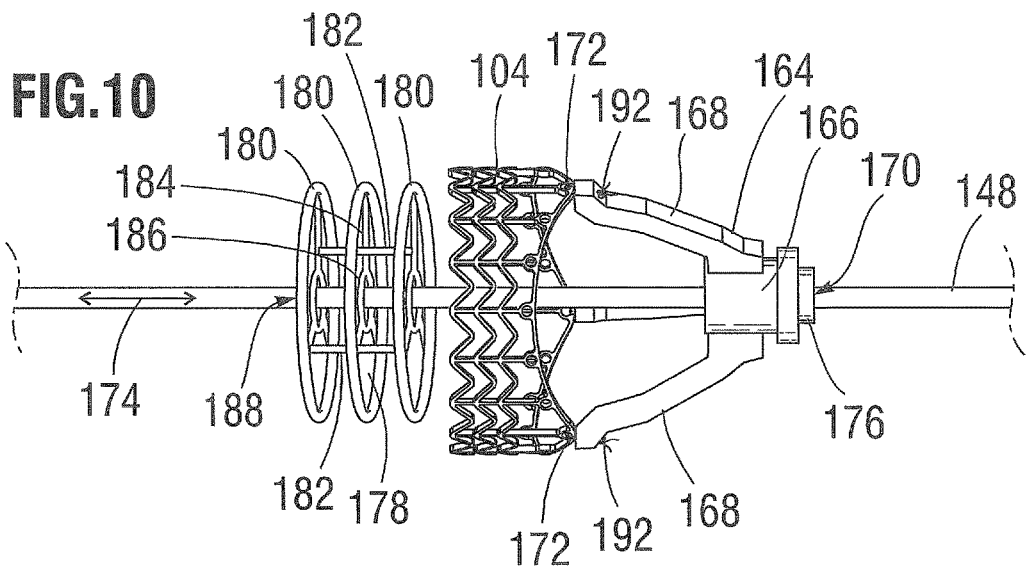
FIG. 10 is a side elevational view of a mandrel for use in the system of FIG. 5, in accordance with one embodiment of the technology described herein, the mandrel holding a secondary frame and a valve holder, which in turn holds a stent.

Referring to FIG. 10 of the illustrative drawings, there is shown an embodiment of a mandrel 148 for use in the system 100, the mandrel holding a stent holder or valve holder 164, which in turn holds a stent 104. The mandrel 148 may be an approximately 3-millimeter stainless-steel rod, although mandrels of different diameters and materials may alternatively be used. In one embodiment, the mandrel 148 has a diameter that is less than the diameter of the stent 104.

Figure 11:
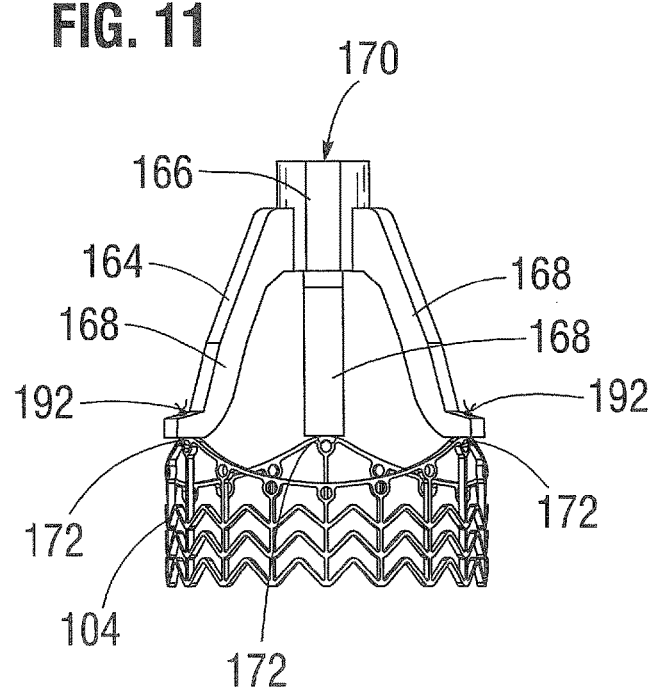
FIG. 11 is a side elevational view of a valve holder sutured to a stent for use in the system of FIG. 5, in accordance with one embodiment of the technology described herein.

The valve holder 164 is used to hold the stent 104. In one embodiment, the stent holder 164 may be a valve holder 22 as shown in FIGS. 1A, 1B, 2A and 2B. The stent holder 164, as seen in FIGS. 10 and 11, includes a central tubular hub portion 166 and a plurality of stabilizing legs 168 projecting axially and radially outward therefrom. In the embodiment shown, the stent holder 164 has three stabilizing legs 168, although a stent holder having greater or fewer stabilizing legs may be used. The central tubular hub portion 166 has an internal bore 170. The stent holder 164 may be formed of a rigid polymer such as acetal (DELRIN®, DuPont), nylon, or polypropylene. The stent 104 is directly secured to the stabilizing legs 168 of the stent holder 164 using sutures 192 at the commissure ends 172 of the stent 104 in the illustrated embodiment, although stent holder and stent are secured using other methods in other embodiments, for example, using pins, clips, clamps, or frictionally.

The stent holder 164 is threaded onto the mandrel 148 via the stent holder's internal bore 170. In one embodiment, the stent holder 164 (and stent 104) may be left free to translate along an axis 174 defined by the mandrel 148. In another embodiment, the stent holder 164 may be secured to the mandrel 148, for example, mechanically or adhesively using an adhesive or adhering means 176 that is non-permanent. Examples of suitable adhesive or adhering means include epoxy and adhesive tape.

In one embodiment, a secondary frame 178 may be additionally threaded onto the mandrel 148 so that the stent 104 is positioned between the secondary frame 178 and the stent holder 164. In the embodiment shown in FIG. 10, the secondary frame 178 comprises a plurality of support elements, which in the illustrated embodiment comprise outer loops 180 connected together by a plurality of connecting wires 182. Each of the plurality of outer loops 180 is connected via a plurality of spokes 184 to one of a plurality of inner loops 186, which are sized and arranged to form an internal bore 188 through which the mandrel 148 may be threaded. Other embodiments use fewer or more support elements, and/or support elements with different diameters, structures (for example, disks), and/or shapes (for example, non-circular). In another embodiment (see, for example, FIG. 13), the secondary frame 178 is a piece of metal or other suitable material, such as stainless steel, ceramic, or polymer, having an internal bore through which the mandrel 148 may be threaded. In one embodiment, the secondary frame 178 has a diameter that is less or smaller than the diameter or inner diameter of the stent 104. In a particular embodiment, the secondary frame 178 extends at least partially within the cavity 103 of the stent 104.

Figure 12:
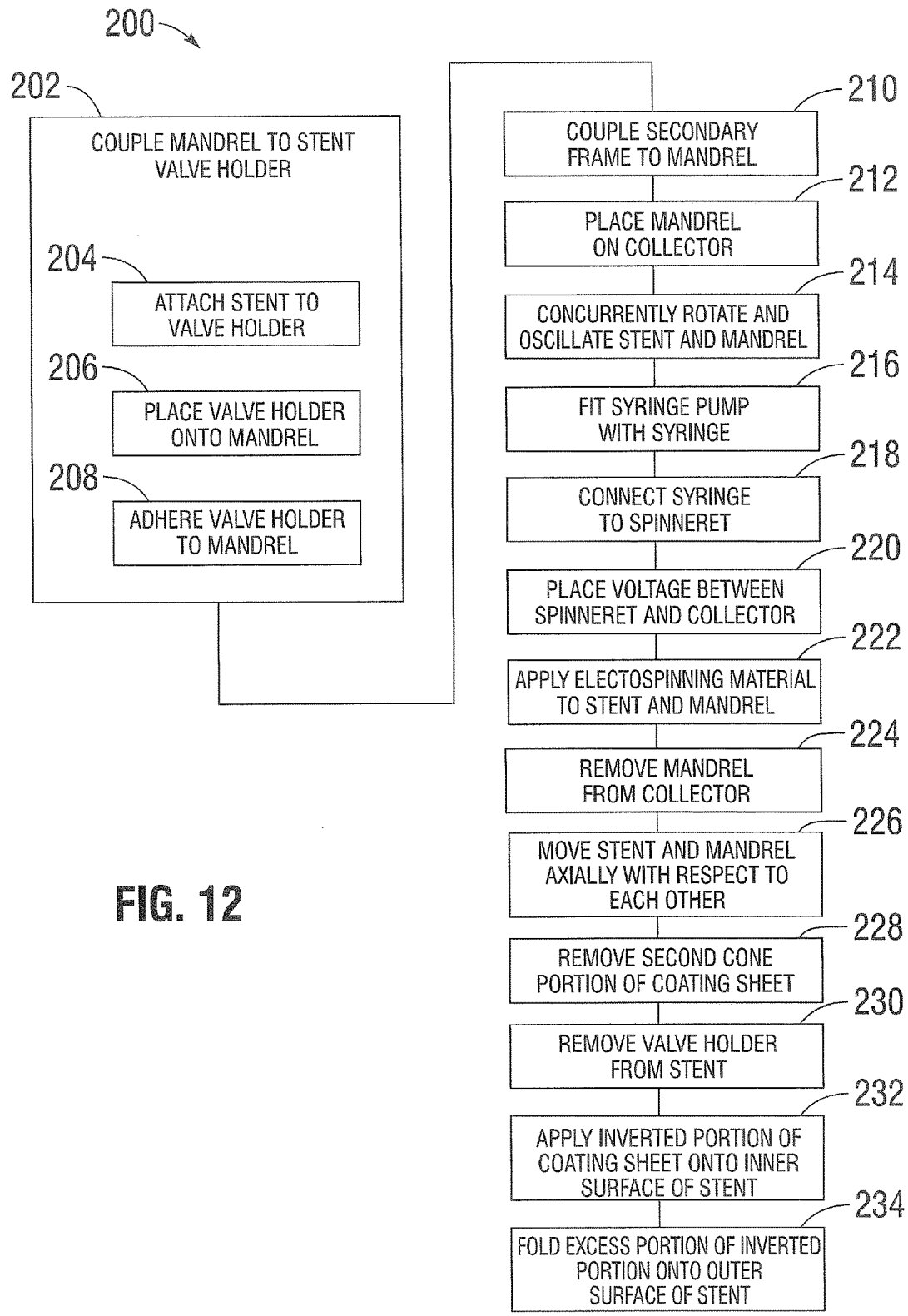
FIG. 12 is a flow chart showing a first method of applying an electrospun material to a stent, in accordance with one embodiment of the technology described herein.

Referring to FIG. 12 of the illustrative drawings, there is shown a method 200 of applying an electrospun material to a stent.

The method comprises a step 202 of coupling a mandrel to a stent body. The stent may be a stent 104 and the mandrel may be a mandrel 148, as described above.

In one embodiment, the step 202 comprises the step 204 of attaching the stent 104 to the stabilizing legs of a stent or valve holder (such as the stent holder 164), for example, as described above using an attaching means, such as sutures at the commissure ends 172 of the stent 104. The step 202 may also comprise the step 206 of placing the stent holder 164 onto the mandrel 148 so that the mandrel extends axially within the stent holder's internal bore 170. In a particular embodiment, the step 204 precedes the step 206, while in another embodiment, the step 206 precedes the step 204.

As described above, the stent holder 164 (and stent 104) may be left free to translate along the axis 174 defined by the mandrel 148. In one embodiment, however, the step 202 further comprises the step 208 of securing the stent holder 164 to the mandrel 148, for example, mechanically or using an adhesive or adhering means 176 that is non-permanent, such as epoxy or adhesive tape, to the mandrel.

In step 210, a secondary frame is coupled to the mandrel 148 so that the stent 104 is positioned between the secondary frame and the stent holder 164. In one embodiment, the secondary frame is the secondary frame 178 shown in FIG. 10. In another embodiment, as shown in FIG. 13, the secondary frame is a piece of metal or other suitable material 300, such as stainless steel, ceramic, or polymer, having an internal bore through which the mandrel 148 may be threaded. At least a portion of the metal piece 300 has a diameter that is less than the diameter or inner diameter of the stent 104 but greater than the diameter of the mandrel 148. In the particular embodiment shown in FIG. 13, the metal piece 300 is positioned with respect to the stent 104 so that a portion of the metal piece extends within the cavity 103 of the stent 104.

In step 212, the mandrel 148 is placed on a collector (such as the collector 108). In one embodiment, the placement of the mandrel 148 on the collector is accomplished by placing the first end 150 of the mandrel in the first collet 144 and the second end 152 of the mandrel in the second collet 146. FIG. 14 shows a collector 108 holding a mandrel 148, a stent holder 164, and a stent 104.

In step 214, the stent 104 and the mandrel 148 are concurrently rotated about and oscillated along the axis 174 defined by the mandrel 148. As described above, the collector 108 may comprise a rotary tool 136 having a rotor motor configured to rotate a collet and a slide motor configured to slide the collet back and forth in an oscillating fashion, with the collet holding an end of the mandrel. The operational parameters of the rotary tool 136 may be controlled by the controller 110.

In step 216, a syringe pump (such as the syringe pump 106) is fitted with a syringe (such as the syringe 112) containing an amount of an electrospinning material (such as the electrospinning material 102). The electrospinning material 102 may be placed in the reservoir 116 of the syringe 112. The syringe 112 may be placed on the syringe holder block 118 of the syringe pump 106 and fixed in place using the syringe clamp 120.

In step 218, the orifice 122 of the syringe 112 is connected via a tube to a spinneret (such as the spinneret 126), with the spinneret positioned and oriented so that the spinneret tip 128 is directed toward the stent 104. In an alternative embodiment, the spinneret 126 is connected directly to the orifice 122 of the syringe 112. The spinneret 126 may be oriented so that it is approximately perpendicular to the axis defined by the mandrel 148.

In step 220, a voltage or potential is placed or applied between the spinneret tip 128 and the collector 108. In one embodiment, the voltage may be applied by connecting the high-voltage power supply 130 by the wires 132 to the spinneret 126 and the collector 108. As part of step 220, the high-voltage power supply 130 may be configured to apply a voltage of about 5 kV to 50 kV. In a particular embodiment, the high-voltage power supply 130 may be configured to apply a voltage of about 14 kV.

In step 222, the electrospinning material 102 is applied to at least a portion of the outer surface 105 of the stent 104 and to at least a portion of the mandrel 148 to form a coating sheet 400. The application of the electrospinning material 102 produces a first cone portion 402 of the coating sheet 400 extending from the second end 404 of the stent 104 to the mandrel 148. FIG. 15 shows such a coating sheet 400 formed on the mandrel 148, the stent holder 164, and the outer surface 105 of the stent 104. The first cone portion 402 of the coating sheet 400 extends from the second end 404 of the stent 104 to the mandrel 148. A second cone portion 406 of the coating sheet 400 extends from the first end 408 of the stent 104 to the central tubular hub portion 166 of the stent holder 164.

In step 224, the mandrel 148 (along with the coated stent 104 and stent holder 164) is removed from the collector 108.

In step 226, one of the stent 104 and the mandrel 148 are moved axially with respect to the other of the stent 104 and the mandrel 148. Alternatively, in step 226, both of the stent 104 and the mandrel 148 may be moved axially with respect to each other. The movement produces an inverted portion 410 of the coating sheet 400 extending inside the cavity 103 of the stent 104 from one of the first end 408 or the second end 404 of the stent. The inverted portion 410 may be formed from the first cone portion 402 or the second cone portion 406 of the coating sheet 400. FIG. 16 shows a coating sheet 400 formed on the mandrel 148, the stent holder 164, and the outer surface 105 of the stent 104. An inverted portion 410 of the coating sheet 400 extends from the second end 404 of the stent 104 to the mandrel 148.

In one embodiment, prior to or after performing the step 226, a step 228 may be performed of removing at least some of the second cone portion 406 of the coating sheet 400. The removal of the second cone portion 406 of the coating sheet 400 may be accomplished by cutting the second cone portion where it meets the first end 408 of the stent 104. The coating sheet on the outer surface 105 of the stent 104 is left undisturbed. FIG. 17 shows a coating sheet 400 formed on the mandrel 148 and the outer surface 105 of the stent 104. The second cone portion 406 of the coating sheet 400 has been removed. An inverted portion 410 of the coating sheet 400 extends from the second end 404 of the stent 104 to the mandrel 148.

Once the step 228 is performed, a step 230 may be performed of removing the stent holder 164 from the stent 104. The removal of the stent holder 164 from the stent 104 may be accomplished by disengaging the members securing the two together, for example, by cutting the sutures 192 at the commissure ends 172 of the stent 104.

In step 232, at least some of the inverted portion 410 of the coating sheet 400 is applied onto the inner surface 101 of the stent 104. In one embodiment, this application is accomplished simply by the movement in step 226 of moving the stent 104 with respect to the mandrel 148 and allowing the inverted portion 410 of the coating sheet 400 to adhere to the inner surface 101 of the stent. In another embodiment, this application is accomplished by a user (for example, manually using fingers) or a tool applying sufficient force to the inverted portion 410 of the coating sheet 400 so that the inverted portion adheres and/or extends along at least a portion of the inner surface 101 of the stent 104. FIG. 18 shows a coating sheet 400 applied to both the inner surface 101 and the outer surface 105 of the stent 104, producing a covered stent 412.

In one embodiment, the method 200 may be repeated to produce a thicker encapsulation of the stent. In another embodiment, the inverted portion 410 of the coating sheet 400 extends beyond the inner surface 101 of the stent 104, forming an excess portion. In this embodiment, the method 200 may further comprise a step 234 of folding the excess portion of the inverted portion 410 back onto the outer surface 105 of the stent 104, producing a second layer of material on the outer surface of the stent and completely encapsulating the stent.

The method 200 thus produces a covered stent 412 that has a consistent inner and outer covering. The method 200 desirably results in less handling of the stent, reduced labor time, and reduced material costs as compared to sewing a pre-made polymeric cloth onto the stent.

Additionally, the method 200 can provide control over the properties of the electrospun material in a way that is not possible with the sewing method. For example, the flowrate of the electrospinning material 102 can be controlled by adjusting the flowrate of the syringe pump 106. The voltage between the spinneret tip 128 and the collector 108 can be controlled by adjusting the voltage applied by the high-voltage power supply 130. The rotational speed of the rotor motor and the oscillation speed of the slide motor in the rotary tool 136 can be controlled by adjusting the rotor speed dial 160 and the slide speed dial 162 on the controller 110.

By controlling the equipment settings and electrospinning time, an operator can produce select for different material properties at localized points, a more streamlined construction that permits increased laminar flow through the stent, and/or a pore size in the coating sheet that permits appropriate tissue ingrowth. In one embodiment, the equipment settings and electrospinning time are adjusted to produce a coating sheet 400 with at least a portion thereof having some combination of: a thickness in the range of from about 0.2 to about 0.8 millimeters, inter-nodular distances in the range of from about 6 to about 80 microns, a tensile strength in the range of from about 15 MPa to about 45 MPa (from about 2500 to about 6500 pounds per square inch), and an average density of from about 0.2 to about 0.5 grams per milliliter.

Figure 19:
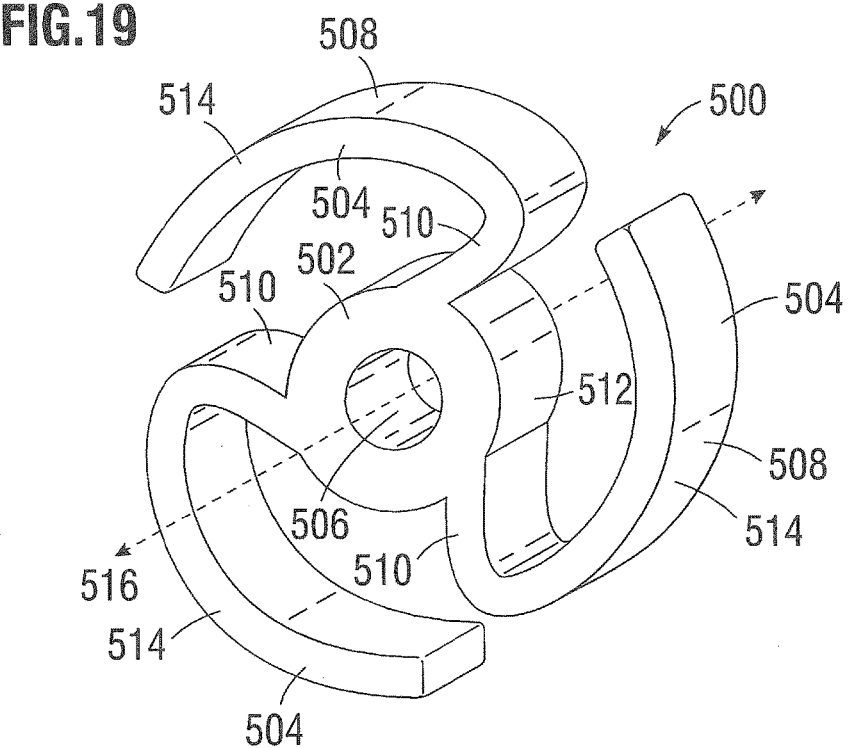
FIG. 19 is a perspective view of an inner holder for holding a stent in accordance with one embodiment of the technology described herein, the inner holder including a central tubular hub portion and a plurality of stabilizing legs projecting outward therefrom.

In one embodiment, instead of using the stent holder 164, an inner holder is used to hold the stent 104. Referring to FIG. 19 of the illustrative drawings, there is shown an embodiment of an inner holder 500 for holding the stent 104. The inner holder 500, as seen in FIG. 19, includes a central tubular hub portion 502 and a plurality of stabilizing legs 504 projecting outward therefrom. In the embodiment shown, the inner holder 500 has three stabilizing legs 504, although an inner holder having greater or fewer stabilizing legs may be used. The central tubular hub portion 502 has an internal bore 506. The inner holder 500 may be formed of metal or a rigid polymer, such as acetal (DELRIN®, DuPont), nylon, or polypropylene. The stent 104 is held by the stabilizing legs 504 of the inner holder 500 by positioning the inner holder in the cavity 103 of the stent and contracting the stent and/or expanding the holder so that at least a portion of the inner surface 101 of the stent contacts an outer surface 508 of the stabilizing legs (see FIG. 20). In other embodiments, the inner holder includes another structure, for example, an expanding mandrel or a balloon.

In one embodiment, each of the plurality of stabilizing legs 504 of the inner holder 500 comprises a radial portion 510 extending in a generally radial direction outward from an outer surface 512 of the central tubular hub portion 502 and an angular portion 514 extending in a generally angular direction about an axis 516 defined by the central tubular hub portion. The outer surface 508 is on the angular portion 514 of the inner holder 500.

Figure 20:
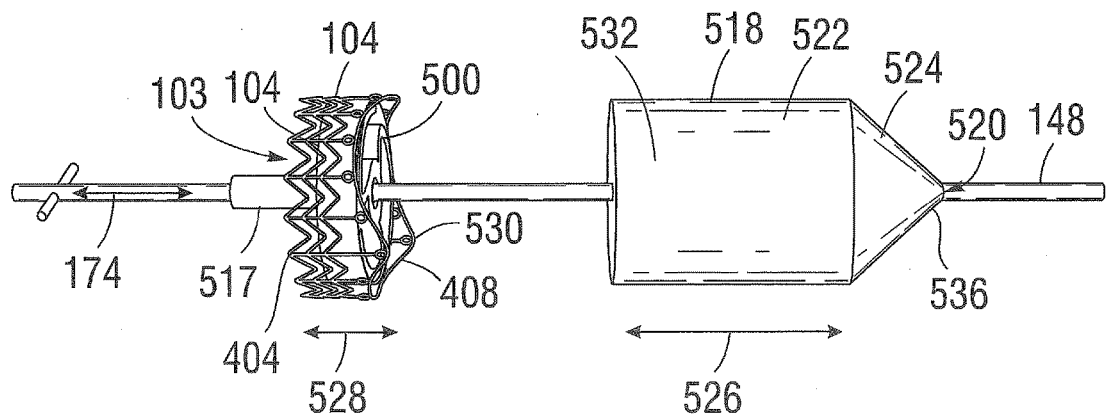
FIG. 20 is a side elevational view of a mandrel on which an inner holder, a stent, and a secondary frame have been threaded, in accordance with one embodiment of the technology described herein.

The inner holder 500 allows the stent 104 to be placed on the mandrel 148 without the use of sutures and lessens interference during the electrospinning steps. Referring to FIG. 20 of the illustrative drawings, the inner holder 500 is threaded onto the mandrel 148 via the inner holder's internal bore 506. In one embodiment, the inner holder 500 (and stent 104) may be left free to translate along the axis 174 defined by the mandrel 148. In another embodiment, the inner holder 500 may be secured to the mandrel 148 mechanically or adhesively, for example, using the adhering means 176. In a further embodiment, the inner holder 500 may be kept in position on the mandrel 148 using a stop or collar, for example, by threading an elastomer tube 517 onto the mandrel (see FIG. 20).

In one embodiment, a secondary frame 518 may be additionally threaded onto the mandrel 148. As shown in FIG. 20, the secondary frame 518 may be threaded onto the mandrel 148 so that the secondary frame is facing the undulating or scalloped first end 408 of the stent 104. In an alternative embodiment, the secondary frame 518 may be threaded onto the mandrel 148 so that the secondary frame is facing the second end 404 of the stent 104. In the embodiment shown in FIG. 20, the secondary frame 518 comprises a suitable material, for example, a piece of metal, such as stainless steel, ceramic, or polymer having an internal bore 520 through which the mandrel 148 may be threaded. In an alternative embodiment, the secondary frame 518 includes a 3D-printed polymer fixture or a balloon. In the embodiment shown in FIG. 20, the secondary frame 518 has a diameter that is less or smaller than the diameter or inner diameter of the stent 104.

In one embodiment, the secondary frame 518 comprises a cylindrical portion 522 and a conical portion 524. The diameter of the cylindrical portion 522 is greater than the diameter of the mandrel 148 and slightly less than the outermost diameter of the inner holder 500. In a particular embodiment, the diameter of the cylindrical portion 522 is approximately 0.8 millimeters to approximately 4 millimeters less than the outermost diameter of the inner holder 500. When used with a coating sheet 400 having a thickness in the range of from about 0.2 to about 0.8 millimeters, such a cylindrical portion diameter permits the axial movement of one or both of the stent 104 and the secondary frame 518 so that at least some of the coating sheet can be applied onto the inner surface 101 of the stent.

In one embodiment, the cylindrical portion 522 of the secondary frame 518 has a length 526 equal to or greater than a length 528 of the stent 104, measured from an eyelet 530 of the first end 408 of the stent to the second end 404 of the stent. In a particular embodiment, the length 526 is equal to or greater than twice the length 528 of the stent 104. Such a cylindrical portion length permits the inverted portion 410 of the coating sheet 400 (originally electrospun onto an outer surface 532 of the secondary frame 518) to extend beyond the inner surface 101 of the stent 104 by an amount sufficient to allow the excess portion to be folded back onto the outer surface 105 of the stent, producing a second layer of material covering the outer surface of the stent when implemented as described below.

Figure 21:
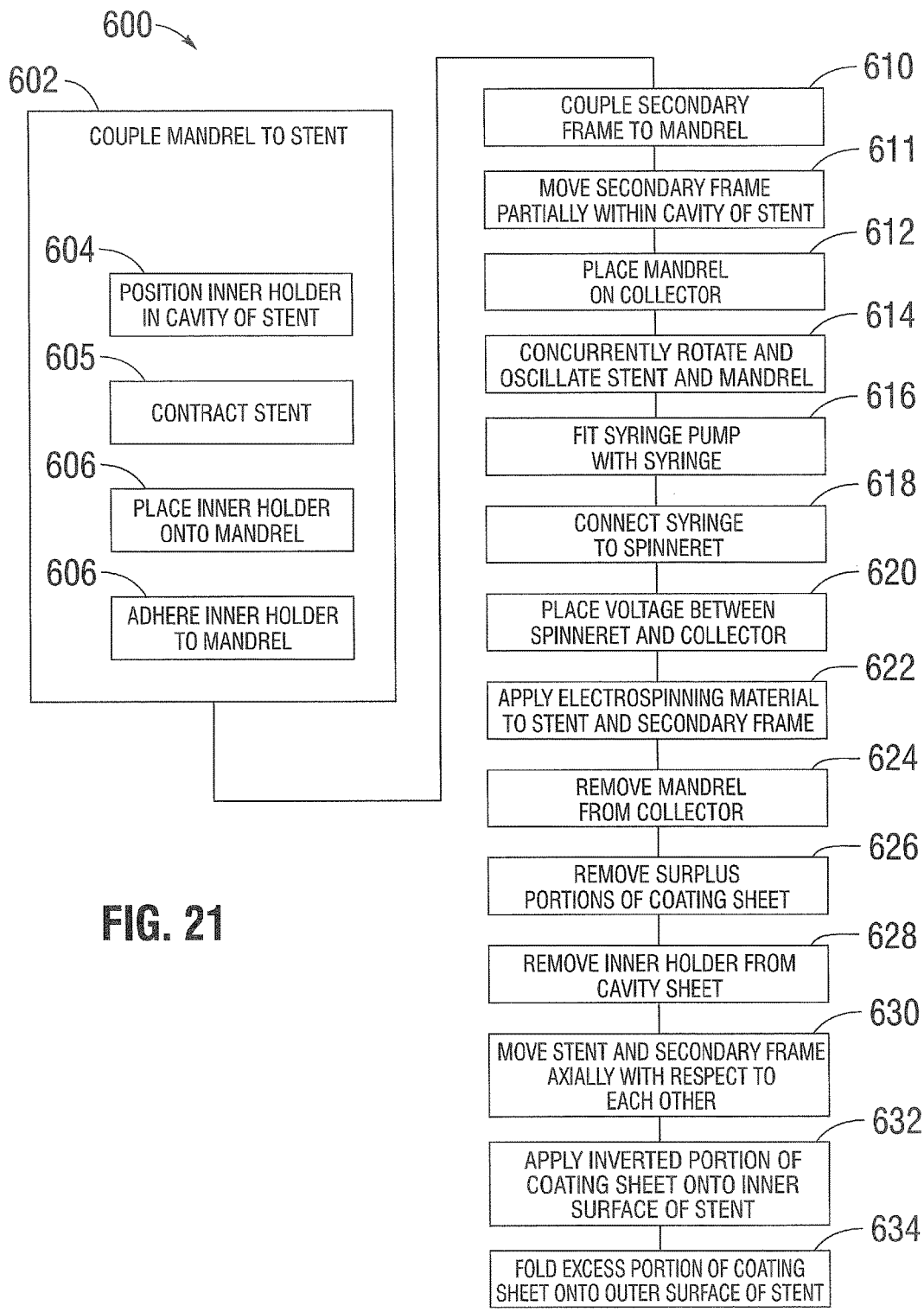
FIG. 21 is a flow chart showing a second method of applying an electrospun material to a stent, in accordance with one embodiment of the technology described herein.

Referring to FIG. 21 of the illustrative drawings, there is shown a method 600 of applying an electrospun material to a stent.

Similar to the method 200, the method 600 comprises a step 602 of coupling a mandrel to a stent body. The stent may be a stent 104 and the mandrel may be a mandrel 148, as described above.

In one embodiment, the step 602 comprises the step 604 of positioning an inner holder (such as the inner holder 500) in the cavity of the stent 104 and the step 605 of contracting the stent so that at least a portion of the inner surface 101 of the stent contacts the outer surface 508 of the stabilizing legs 504 of the inner holder 500 (see FIG. 20). The step 602 may also comprise the step 606 of placing the inner holder 500 onto the mandrel 148 so that the mandrel extends axially within the inner holder's internal bore 506. In a particular embodiment, the steps 604 and 605 precede the step 606, while in another embodiment, the step 606 precedes the steps 604 and 605.

As described above, the inner holder 500 (and stent 104) may be left free to translate along the axis 174 defined by the mandrel 148. In one embodiment, however, the step 602 further comprises the step 608 of securing the inner holder 500 to the mandrel 148 mechanically or adhesively, for example, by adding an adhering means 176 that is non-permanent, such as epoxy or adhesive tape, to the mandrel.

In step 610, a secondary frame is coupled to the mandrel 148 so that the secondary frame is facing the undulating or scalloped first end 408 of the stent 104. In an alternative embodiment, the secondary frame may be threaded onto the mandrel 148 so that the secondary frame is facing the second end 404 of the stent 104. In one embodiment, the secondary frame is the secondary frame 518 shown in FIG. 20.

Figure 22:
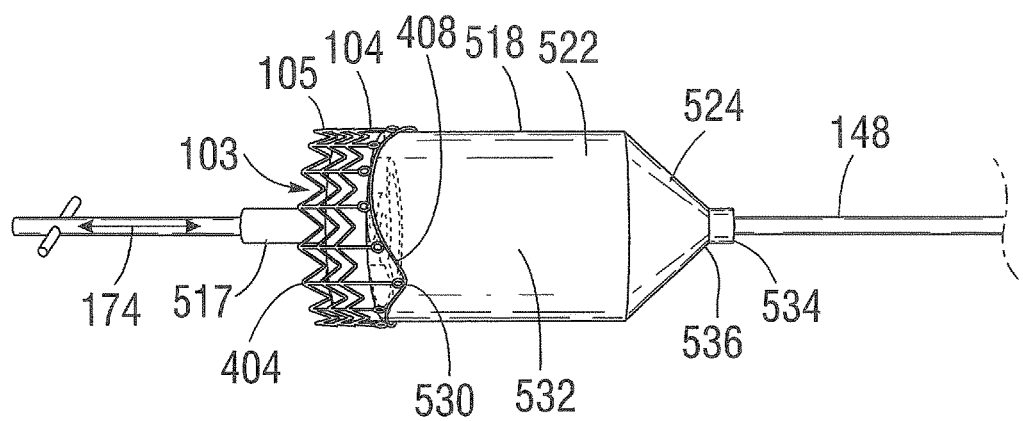
FIG. 22 is a side elevational view of a mandrel on which an inner holder, a stent, and a secondary frame have been threaded so that the secondary frame extends at least partially within the cavity of the stent, in accordance with one embodiment of the technology described herein.

In step 611, the secondary frame 518 moved with respect to the stent 104 so that the secondary frame 518 extends at least partially within the cavity 103 of the stent 104. FIG. 22 shows a mandrel 148 on which an inner holder 500, a stent 104, and a secondary frame 518 have been threaded so that the secondary frame extends at least partially within the cavity 103 of the stent. An stop or collar, for example, an elastomer ring 534, may additionally be threaded onto the mandrel 148 and positioned adjacent an apex 536 of the conical portion 524 of the secondary frame 518 to keep the secondary frame in position on the mandrel.

In step 612, similar to the step 212, the mandrel 148 is placed on a collector (such as the collector 108). In one embodiment, the placement of the mandrel 148 on the collector is accomplished by placing the first end 150 of the mandrel in the first collet 144 and the second end 152 of the mandrel in the second collet 146.

In step 614, similar to the step 214, the stent 104 and the mandrel 148 are concurrently rotated about and oscillated along the axis 174 defined by the mandrel 148. As described above, the collector 108 may comprise a rotary tool 136 having a rotor motor configured to rotate a collet and a slide motor configured to slide the collet back and forth in an oscillating fashion, with the collet holding an end of the mandrel. The rotary tool 136 may be controlled by the controller 110.

In step 616, similar to the step 216, a syringe pump (such as the syringe pump 106) is fitted with a syringe (such as the syringe 112) containing an amount of an electrospinning material (such as the electrospinning material 102). The electrospinning material 102 may be placed in the reservoir 116 of the syringe 112. The syringe 112 may be placed horizontally on the syringe holder block 118 of the syringe pump 106 and fixed in place using the syringe clamp 120.

In step 618, similar to the step 218, the orifice 122 of the syringe 112 is connected via a tube to a spinneret (such as the spinneret 126), with the spinneret positioned and oriented so that the spinneret tip 128 is directed toward the stent 104. In an alternative embodiment, the spinneret 126 is connected directly to the orifice 122 of the syringe 112. The spinneret 126 may be oriented so that it is approximately perpendicular to the axis defined by the mandrel 148.

In step 620, similar to the step 220, a voltage is placed or applied between the spinneret tip 128 and the collector 108. In one embodiment, the voltage may be placed by connecting the high-voltage power supply 130 by the wires 132 to the spinneret 126 and the collector 108. As part of step 220, the high-voltage power supply 130 may be configured to apply a voltage of about 5 kV to 50 kV. In a particular embodiment, the high-voltage power supply 130 may be configured to apply a voltage of about 14 kV.

Figure 23:
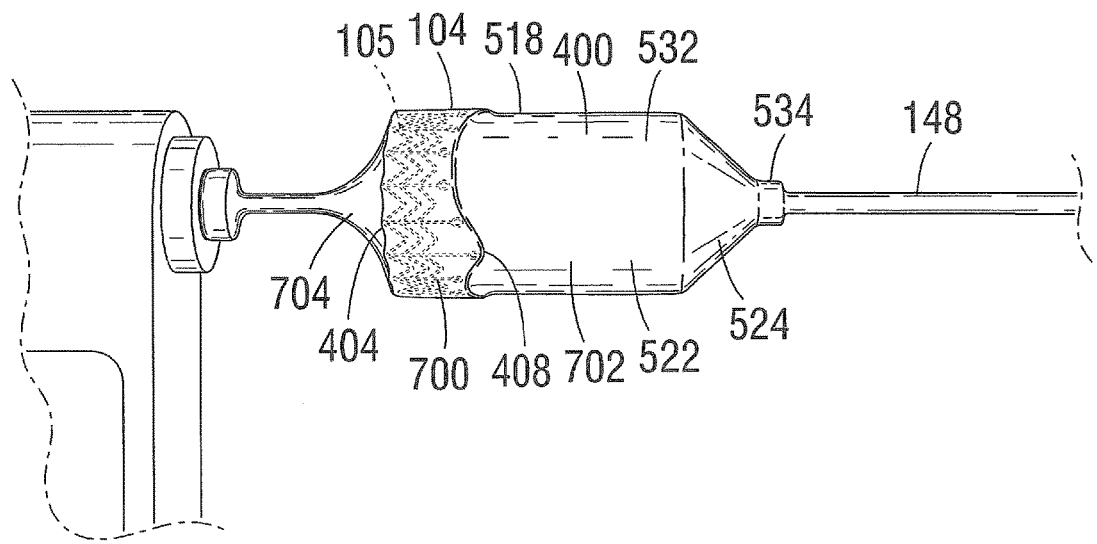
FIG. 23 is a side elevational view of a mandrel, a stent, and a secondary frame on which a coating sheet has been formed, in accordance with one embodiment of the technology described herein.

In step 622, the electrospinning material 102 is applied to at least a portion of the outer surface 105 of the stent 104 and to at least a portion of the secondary frame 518 to form a coating sheet 400. The application of the electrospinning material 102 produces a first portion 700 of the coating sheet 400 on the outer surface 105 of the stent 104 and a second portion 702 of the coating sheet on the outer surface 532 of the secondary frame 518. FIG. 23 shows such a coating sheet 400 formed on the mandrel 148, the outer surface 532 of the secondary frame 518, and the outer surface 105 of the stent 104. A cone portion 704 of the coating sheet 400 extends from the second end 404 of the stent 104 to the mandrel 148.

In step 624, the mandrel 148 (along with the coated stent 104, the inner holder 500 and the coated secondary frame 518) is removed from the collector 108.

In step 626, the cone portion 704 and other surplus portions of the coating sheet 400 beyond the first portion 700 and the second portion 702 are removed. The removal of the surplus portions of the coating sheet 400 may be accomplished, for example, by cutting the coating sheet at the apex 536 of the conical portion 524 of the secondary frame 518, and at the second end 404 of the stent 104. The first portion 700 and the second portion 702 are left undisturbed. FIGS. 24 and 25 show a coating sheet 400 formed on the mandrel 148, the outer surface 532 of the secondary frame 518, and the outer surface 105 of the stent 104. The cone portion 704 and other surplus portions of the coating sheet 400 beyond the first portion 700 and the second portion 702 have been removed.

In step 628, the inner holder 500 is removed from the cavity 103 of the stent 104.

In step 630, one of the stent 104 and the secondary frame 518 are moved axially with respect to the other of the stent 104 and the secondary frame 518. Alternatively, in step 630, both of the stent 104 and the secondary frame 518 may be moved axially with respect to each other. The movement produces an inverted portion 410 of the coating sheet 400 extending inside the cavity 103 of the stent 104 from the first end 408 of the stent. The inverted portion 410 may be formed from the second portion 702 of the coating sheet 400. In one embodiment, steps 628 and 630 are combined, with the secondary frame 518 pushing the inner holder 500 out of the cavity 103 of the stent 104 as the secondary frame is moved.

In step 632, similar to the step 232, at least some of the inverted portion 410 of the coating sheet 400 is applied onto the inner surface 101 of the stent 104. In one embodiment, this application is accomplished simply by the movement in step 630 of moving the stent 104 with respect to the secondary frame 518 and allowing the inverted portion 410 of the coating sheet 400 to adhere to the inner surface 101 of the stent. In another embodiment, this application is accomplished by a user (for example, manually using fingers) or a tool applying a sufficient force to the inverted portion 410 of the coating sheet 400 so that the inverted portion extends along and/or adheres to at least a portion of the inner surface 101 of the stent 104. FIG. 26 shows a coating sheet 400 applied to both the inner surface 101 and the outer surface 105 of the stent 104, producing a covered stent having an excess portion 706 of the coating sheet 400 extending beyond the second end 404 of the stent.

In step 634, the excess portion 706 of the coating sheet 400 is folded back onto or over the outer surface 105 of the stent 104, producing a second layer of material on the outer surface of the stent and completely encapsulating the stent. The method 600 may be repeated to produce a thicker encapsulation of the stent.

Figure 27:
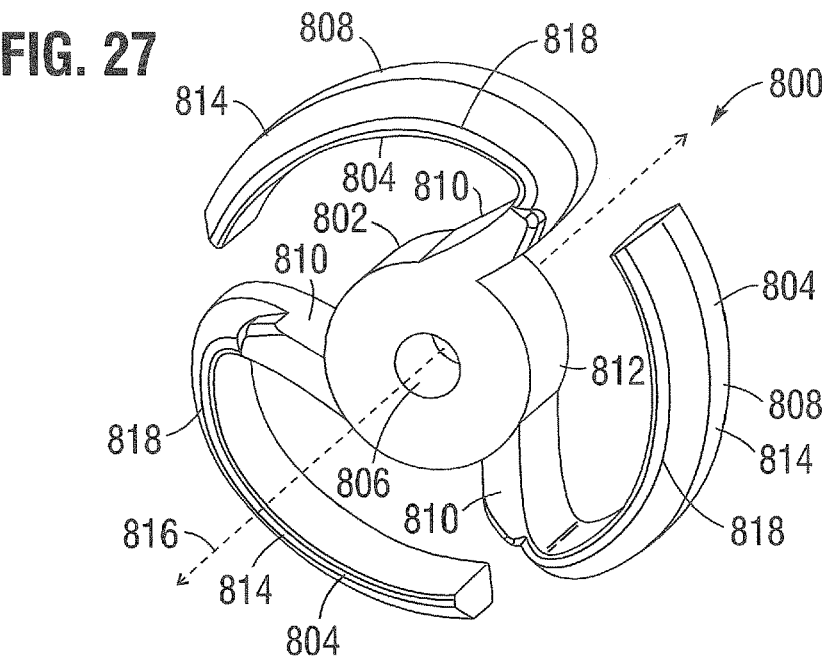
FIG. 27 is a perspective view of an alternative embodiment of an inner holder for holding a stent in accordance with one embodiment of the technology described herein, the inner holder including a central tubular hub portion and a plurality of stabilizing legs projecting outward therefrom, with chamfered edges extending from the stabilizing legs.

Referring to FIG. 27 of the illustrative drawings, there is shown an embodiment of an inner holder 800 for holding the stent 104. The inner holder 800 may be an alternative embodiment of the inner holder 500, as shown in FIG. 19. The inner holder 800, as seen in FIG. 27, includes a central tubular hub portion 802 and a plurality of stabilizing legs 804 projecting outward therefrom. In the embodiment shown, the inner holder 800 has three stabilizing legs 804, although an inner holder having greater or fewer stabilizing legs may be used. The central tubular hub portion 802 has an internal bore 806. The inner holder 800 may be formed of metal or a rigid polymer, such as acetal (DELRIN®, DuPont), nylon, or polypropylene. The stent 104 is held by the stabilizing legs 804 of the inner holder 800 by positioning the inner holder in the cavity 103 of the stent 104 and contracting the stent 104 and/or expanding the holder 800 so that at least a portion of the inner surface 101 of the stent 104 contacts an outer surface 808 of the stabilizing legs 804 (see FIG. 28). In other embodiments, the inner holder includes another structure, for example, an expanding mandrel or a balloon.

In one embodiment, each of the plurality of stabilizing legs 804 of the inner holder 800 comprises a radial portion 810 extending in a generally radial direction outward from an outer surface 812 of the central tubular hub portion 802 and an angular portion 814 extending in a generally angular direction about an axis 816 defined by the central tubular hub portion 802. The outer surface 808 is on the angular portion 814 of the inner holder 800.

In one embodiment, each of the plurality of stabilizing legs 804 comprises a chamfered edge 818 extending along each angular portion 814, facing one side of the inner holder 800. In one embodiment, the chamfered edge 818 aligns an inner edge of each angular portion 814, extending from the radial portion 810 all the way to the tip of the angular portion 814, as seen in FIG. 27. In one embodiment, the width of the angular portion 814 with the chamfered edge 818 is equal to or less than the width of the radial portion 810. In one embodiment, the chamfered edge 818 may have a constant width along its length, or the width may vary. In other embodiments, the chamfered edge 818 may be segmented, or may have other shapes, sizes, and/or locations.

Figure 28:
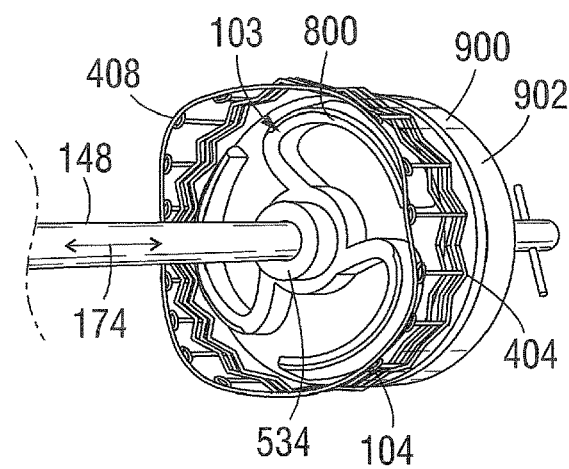
FIG. 28 is a perspective view of a mandrel on which an inner holder, a stent, and an auxiliary holder have been threaded, in accordance with one embodiment of the technology described herein.

The inner holder 800 allows the stent 104 to be placed on the mandrel 148 without the use of sutures and lessens interference during the electrospinning steps. Referring to FIG. 28 of the illustrative drawings, the inner holder 800 is threaded onto the mandrel 148 via the inner holder's internal bore 806. In one embodiment, the inner holder 800 (and stent 104) may be left free to translate along the axis 174 defined by the mandrel 148. In another embodiment, the inner holder 800 may be secured to the mandrel 148 mechanically or adhesively, for example, using the adhering means 176. In a further embodiment, the inner holder 800 may be kept in position on the mandrel 148 using a stop or collar, for example, by threading an elastomer ring 534 onto the mandrel 148 (see FIG. 28).

FIG. 28 also demonstrates an embodiment of an auxiliary frame 900 for assisting the cutting of the coating sheet. In one embodiment, the auxiliary frame 900 is threaded onto the mandrel 148 before threading the inner holder 800 onto the mandrel 148, so that the auxiliary frame 900 is facing the second end 404 of the stent 104. In one embodiment, the auxiliary frame 900 comprises a suitable material, for example, a piece of metal, such as stainless steel, ceramic, or polymer having an internal bore through which the mandrel 148 may be threaded. A stop or collar, for example, an elastomer ring 534, may be threaded onto the mandrel 148 and positioned on either or both sides of the auxiliary frame 900 to keep the auxiliary frame 900 in position on the mandrel 184. In one embodiment, the inner holder 800 and the auxiliary frame 900 may be spaced on the mandrel 148 by one or more elastomer rings 534 (see FIG. 29). In one embodiment, the diameter of the auxiliary frame 900 is greater than the diameter of the mandrel 148 and approximately equal to or slightly more than the outermost diameter of the inner holder 800. The auxiliary frame 900 has an outer surface 902 that may or may not be in contact with the stent 104. As shown in FIG. 28, the outer surface 902 is spaced from the stent 104 to assist with the cutting of the coating sheet between the auxiliary frame 900 and the stent 104.

Figure 29:
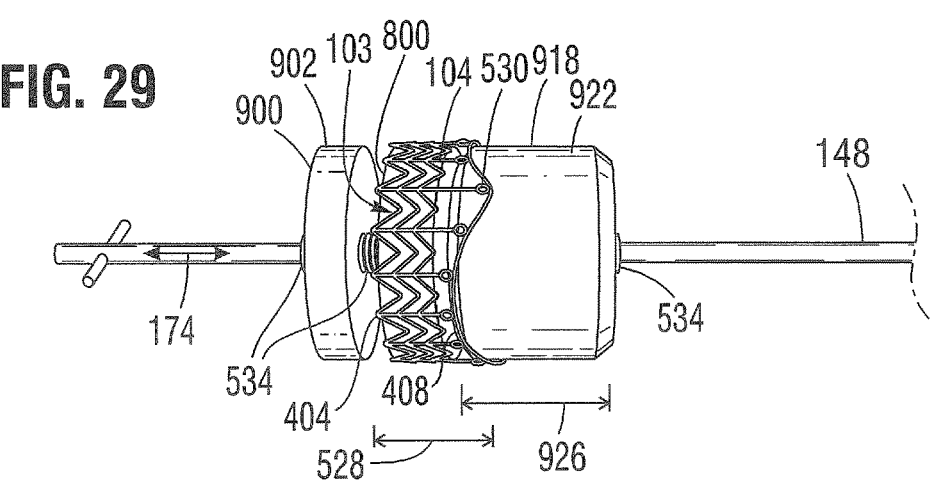
FIG. 29 is a side elevational view of a mandrel on which an inner holder, a stent, an auxiliary holder, and a secondary frame have been threaded so that the secondary frame extends at least partially within the cavity of the stent, in accordance with one embodiment of the technology described herein.

As shown in FIG. 29 of the illustrative drawings, an embodiment of a secondary frame 918 is threaded onto the mandrel 148 so that the secondary frame 918 is facing the undulating or scalloped first end 408 of the stent 104. In an alternative embodiment, the secondary frame 918 may be threaded onto the mandrel 148 so that the secondary frame 918 is facing the second end 404 of the stent 104. In the embodiment shown in FIG. 29, the secondary frame 918 comprises a suitable material, for example, a piece of metal, such as stainless steel, ceramic, or polymer having an internal bore through which the mandrel 148 may be threaded. In an alternative embodiment, the secondary frame 918 includes a 3D-printed polymer fixture or a balloon. In the embodiment shown in FIG. 29, the secondary frame 918 has a diameter that is less or smaller than the diameter or inner diameter of the stent 104.

In one embodiment, the secondary frame 918 comprises a cylindrical portion 922. In one embodiment, the secondary frame 918 is similar to the secondary frame 518 as shown in FIG. 22, except that the secondary frame 918 at an end does not comprise a conical portion. The diameter of the cylindrical portion 922 is greater than the diameter of the mandrel 148 and slightly less than the outermost diameter of the inner holder 800. In a particular embodiment, the diameter of the cylindrical portion 922 is approximately 0.8 millimeters to approximately 4 millimeters less than the outermost diameter of the inner holder 800. When used with a coating sheet 400 having a thickness in the range of from about 0.2 to about 0.8 millimeters, such a cylindrical portion diameter permits the axial movement of one or both of the stent 104 and the secondary frame 918 so that at least some of the coating sheet can be applied onto the inner surface 101 of the stent 104.

In one embodiment, the cylindrical portion 922 of the secondary frame 918 has a length 926 equal to or greater than a length 528 of the stent 104, measured from an eyelet 530 of the first end 408 of the stent to the second end 404 of the stent. In a particular embodiment, the length 926 is equal to or greater than twice the length 528 of the stent 104. Such a cylindrical portion length permits an inverted portion (such as the inverted portion 410) of the coating sheet 400 (originally electrospun onto an outer surface of the secondary frame 918) to extend beyond the inner surface 101 of the stent 104 by an amount sufficient to allow the excess portion to be folded back onto the outer surface 105 of the stent, producing a second layer of material covering the outer surface 105 of the stent when implemented as described below. A stop or collar, for example, an elastomer ring 534, may additionally be threaded onto the mandrel 148 and positioned adjacent an end of the secondary frame 918 to keep the secondary frame 918 in position on the mandrel 184.

FIG. 30 shows that a coating sheet 400 is formed on the mandrel 148, the outer surface 932 of the secondary frame 918, the outer surface 105 of the stent 104, and the outer surface 902 of the auxiliary frame 900. Cone portions 704 and 710 of the coating sheet 400 extend from the end of the auxiliary frame 900 and the end of the secondary frame 918 to the mandrel 148, respectively.

FIG. 31 shows that the cone portion 704 and other surplus portions of the coating sheet 400 beyond the second end 404 of the stent are removed. In one embodiment, the removal of the surplus portions of the coating sheet 400 beyond the second end 404 of the stent may be accomplished by cutting the coating sheet 400 on the auxiliary frame 900 where it meets the first end 408 of the stent 104. Alternatively, the cutting of the coating sheet 400 is at the space between the auxiliary frame 900 and the inner holder 800 or the second end 404 of the stent. The coating sheet 400 on the outer surface 105 of the stent 104 is left undisturbed. In one embodiment, before removing the surplus portions of the coating sheet 400, the mandrel 148 (along with the coated stent 104, the inner holder 800, the coated secondary frame 918, and the coated auxiliary frame 900) is removed from the collector 108.

As shown in FIG. 32, the cone portion 710 and other surplus portions of the coating sheet 400 beyond the end of the cylindrical portion 922 of the secondary frame are also removed. In one embodiment, the removal of the surplus portions of the coating sheet 400 beyond the end of the cylindrical portion 922 may be accomplished by cutting the cone portion 710 where it meets the cylindrical portion 922.

In one embodiment, after the cone portions 704 and 710 and other surplus portions of the coating sheet 400 are removed, the mandrel 184 and the auxiliary frame 900 are removed, and the inner holder 800 is removed from the cavity 103 of the stent 104. In one embodiment, one of the stent 104 and the secondary frame 918 are moved axially with respect to the other of the stent 104 and the secondary frame 918. Alternatively, both of the stent 104 and the secondary frame 918 may be moved axially with respect to each other. The movement produces an inverted portion (such as the inverted portion 410) of the coating sheet 400 extending inside the cavity 103 of the stent 104 from the first end 408 of the stent. The inverted portion may be formed from the second portion 702 of the coating sheet 400. In one embodiment, the secondary frame 918 pushes the inner holder 800 out of the cavity 103 of the stent 104 as the secondary frame 918 is moved.

In one embodiment, similar to FIG. 26, at least some of the inverted portion of the coating sheet 400 is applied onto the inner surface 101 of the stent 104. In one embodiment, this application is accomplished simply by the movement of the stent 104 with respect to the secondary frame 918 and allowing the inverted portion of the coating sheet 400 to adhere to the inner surface 101 of the stent. In another embodiment, this application is accomplished by a user (for example, manually using fingers) or a tool applying a sufficient force to the inverted portion of the coating sheet 400 so that the inverted portion extends along and/or adheres to at least a portion of the inner surface 101 of the stent 104. In one embodiment, the coating sheet 400 is applied to both the inner surface 101 and the outer surface 105 of the stent 104, producing a covered stent 104 having an excess portion (such as the excess portion 706) of the coating sheet 400 extending beyond the second end 404 of the stent. In one embodiment, the excess portion of the coating sheet 400 is folded back onto or over the outer surface 105 of the stent 104, producing a second layer of material on the outer surface of the stent 104 and completely encapsulating the stent 104. An embodiment of a completely encapsulated stent 104 on the second frame 918 is shown in FIG. 35, with the edge 711 of the folded second layer of material on the outer surface of the stent 104.

Figure 33:
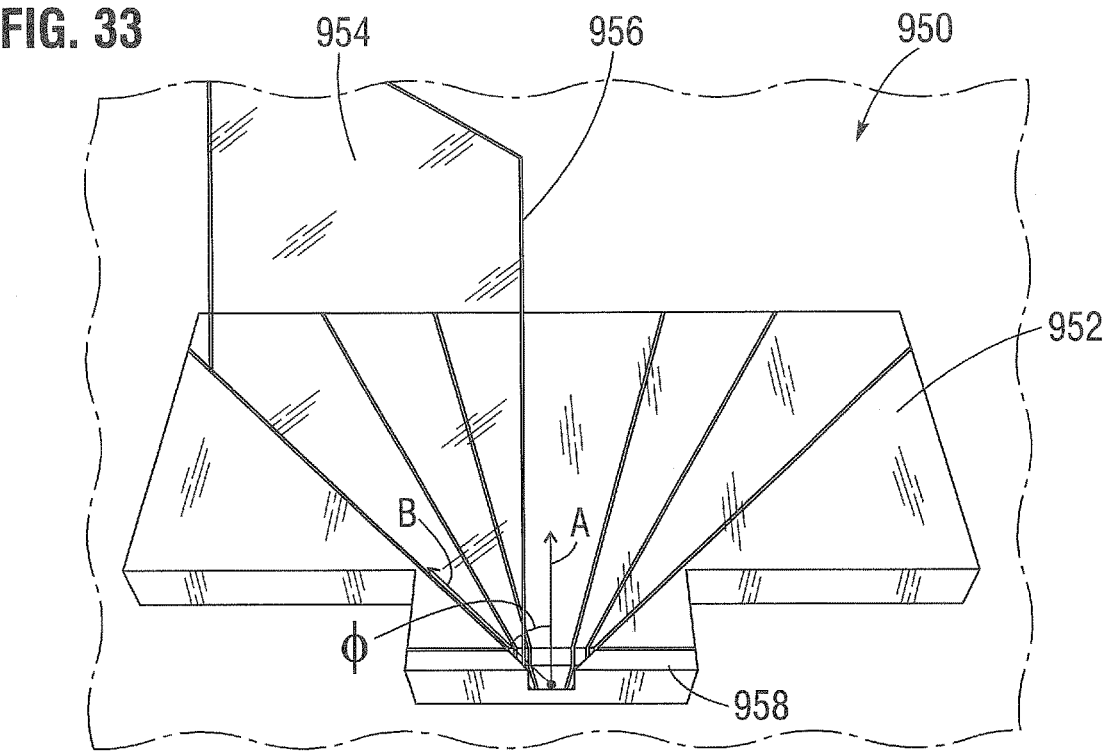
FIG. 33 is a perspective view of a filter held by a filter base, in accordance with one embodiment of the technology described herein, with adjustable angles of the filter with respect to an axis of the filter base.

Referring to FIG. 33 of the illustrative drawings, there is shown an embodiment of a filter device 950 that comprises a filter 954 held by a filter base 952. In one embodiment, the filter 954 comprises a solid rectangular sheet, although other shapes may alternatively be used. In one embodiment, the filter 954 comprises a suitable material, for example, a piece of glass or plastic. In one embodiment, the filter 954 is fitted into one of a plurality of grooves on the top surface of the filter base 952, while each groove serves to stabilize the filter 954 and to keep the filter 954 perpendicular to the top surface of the filter base 952. In one embodiment, the filter base 952 includes an extension portion 958 extending from the middle on one side of the base 952, in the same plane as the base 952. The grooves extend radially from the middle of the edge of the extension portion 958 toward the sides of the base 952 (see FIG. 33). When fitted in one of the grooves, one edge 956 of the filter 954 is adjacent to and perpendicular to the edge of the extension portion 958. An axis A of the base 952 is defined as the direction perpendicular to the edge of the extension portion 958 from which the grooves extend. An angle $\Phi$ of the filter 954 fitted in a groove is defined by the angle of the direction B of the groove from the axis A. The angle of the filter 954 is thus adjustable via fitting the filter 954 in a selected groove. FIG. 33 shows six grooves symmetrically located on either side of the axis A, although other numbers of grooves, symmetrically or non-symmetrically arranged, may alternatively be used. In one embodiment, the angles $\Phi$ of the filter 954 may be selected from, for example, 85, 80, 75, 70, 65, 60, 55, 50, 45, 40, 35, 30, 25, 20, 15, 10, or 5 degrees. In another embodiment, another structure may be used to hold the filter 954 at different angles, for example, a hinged structure that permits the filter to be positioned at a desired angle.

Figure 34:
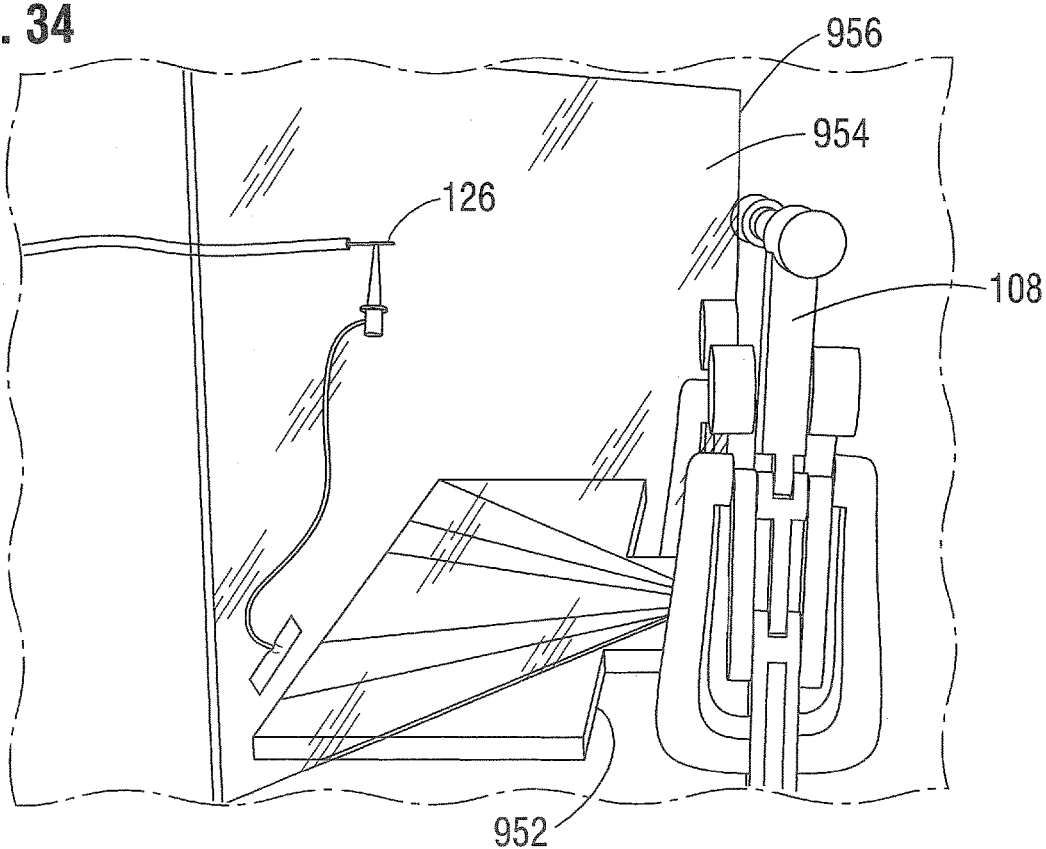
FIG. 34 is a side elevational view of a collector for use in the system of FIG. 5 in accordance with one embodiment of the technology described herein, the collector having a mandrel on which an inner holder, a stent, an auxiliary holder, and a secondary frame have been threaded and a filter is positioned between the stent and the spinneret.

FIG. 34 shows that, in a system similar to that of FIG. 5, the filter 954 with the base 952 is positioned between the spinneret 126 and the collector having a mandrel 184, a secondary frame 918, and an encapsulated stent 104 thereon. The edge 956 of the filter 954 is positioned adjacent to the stent 104, with a portion on one side of the filter 954 and the other portion on the other side. In one embodiment, one portion of the stent 104 is on the same side of the filter 954 as the spinneret 126, and thus is exposed to the spinneret 126 and can be electrospun. The other portion of the stent 104 on the other side of the filter 954 is covered/blocked by the filter 954, and thus cannot be electrospun.

Figure 35:
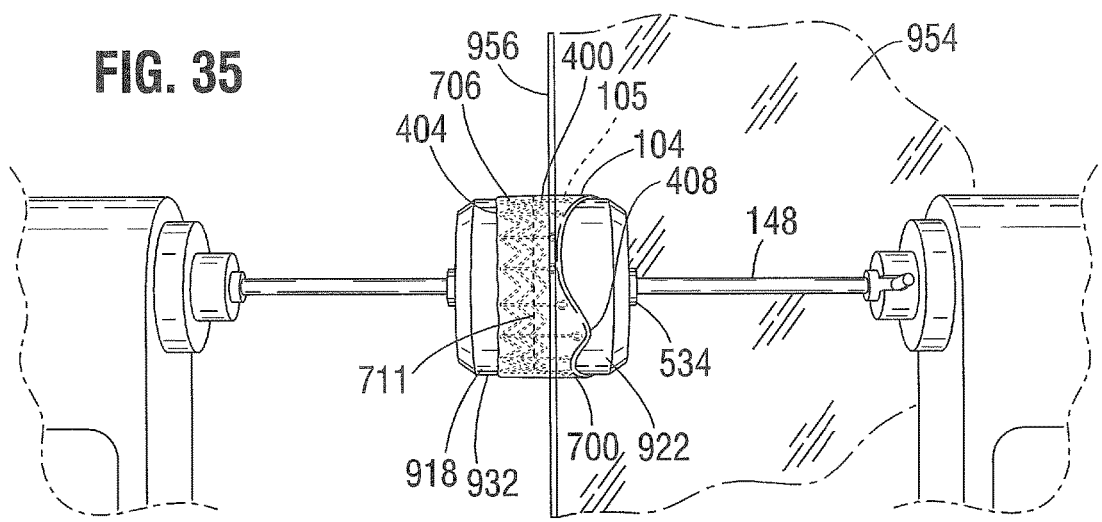
FIG. 35 is a perspective view of a mandrel and a secondary frame with an encapsulated stent thereon, in accordance with one embodiment of the technology described herein, with the filter positioned to a portion of the encapsulated stent on an exposed side of the filter.

As shown in FIG. 35, the mandrel 148, on which the secondary frame 918 with encapsulated stent 104 thereon is threaded, is connected to the collector. The filter 954 is positioned so that the edge 956 is between the first end 408 and second end 404 of the stent 104. The edge 711 of the folded second layer of the excess portion (such as the excess portion 706) on the outer surface of the encapsulated stent 104 is on the exposed side of the filter 954. In one embodiment, the angle $\Phi$ of the filter 954 is about 45 degrees, although other angles may be alternatively used.

Figure 36:
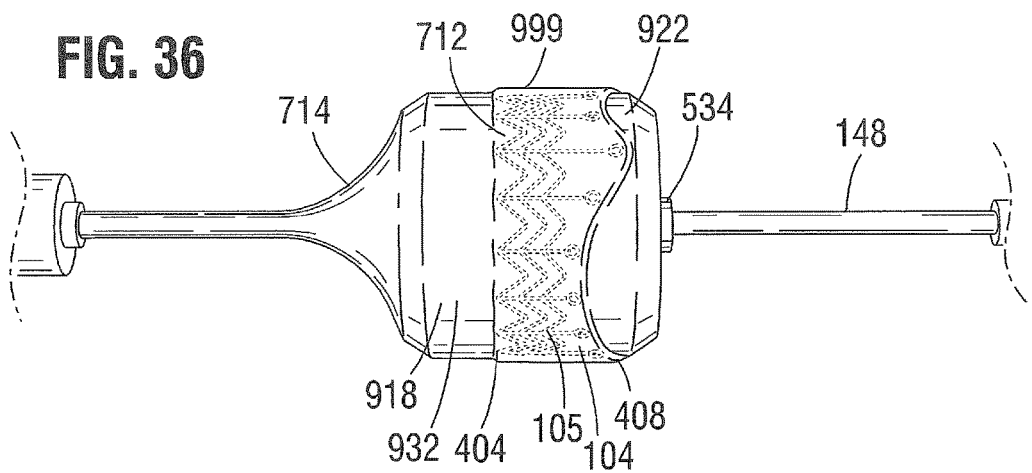
FIG. 36 is a side elevational view of a mandrel and a secondary frame with an encapsulated stent thereon, on which a coating sheet has been formed on an exposed side of a filter, in accordance with one embodiment of the technology described herein.
Figure 37:
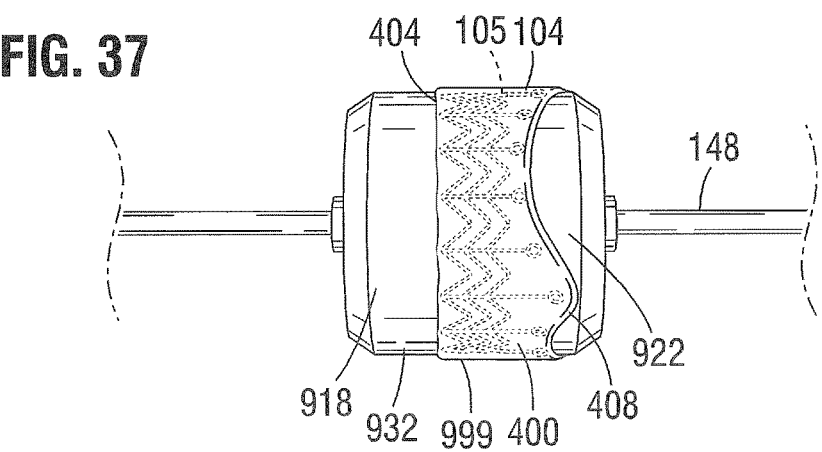
FIG. 37 is a side elevational view of a mandrel and a secondary frame with an encapsulated stent thereon, on which a coating sheet has been formed on an exposed side of a filter, in accordance with one embodiment of the technology described herein, with surplus portions of the coating sheet having been removed.

FIG. 36 shows a coating sheet 999 formed on the mandrel 148, a portion of the outer surface 932 of the secondary frame 918, and the exposed portion of the encapsulated stent 104. In one embodiment, as shown in FIG. 36, the coating sheet 999 covers the edge 711 of the folded second layer of the excess portion. A cone portion 714 of the coating sheet 999 extends from the end of the secondary frame 918 to the mandrel 148. The cone portion 714 and other surplus portions of the layer of coating sheet 999 beyond the second end 404 of the stent 104 are removed, as shown in FIG. 37. The removal of the cone portion 714 and surplus portions of the coating sheet 999 may be accomplished, for example, by cutting the coating sheet 999 at the second end 404 of the stent 104. The layer of coating sheet 999 that covers the exposed portion of the encapsulated stent 104 is left undisturbed. In one embodiment, the mandrel 184 is removed from the collector before removal of the cone portion 714 and surplus portions of the coating sheet 999.

Referring to FIG. 38 of the illustrative drawings, there is shown a method 1000 of applying an extra layer of electrospun material to the encapsulated stent 104. In one embodiment, the extra layer of material may cover the edge (such as the edge 711) of the folded second layer of the excess portion (such as the excess portion 706) on the outer surface of the encapsulated stent 104.

In step 1001, the mandrel 148 that has the secondary frame 918 and the encapsulated stent 104 thereon is placed on a collector (such as the collector 108). In one embodiment, the placement of the mandrel 148 on the collector is accomplished in a similar manner as described in the step 612.

In step 1002, the filter 954 is placed between the spinneret (such as the spinneret 126) and the collector, while the edge 956 of the filter 954 is adjacent to the encapsulated stent 104 and perpendicular to the axis 174 defined by the mandrel 148. In one embodiment, the filter 954 held by the base 952 is positioned at an angle Φ (see FIG. 33), while the spinneret 126 is at one side of the filter 954, referred to as the "exposed side".

In step 1003, the position of the edge 956 of the filter is adjusted such that a portion of the encapsulated stent 104 that comprises the edge 711 of the folded portion is at the exposed side of the filter 954.

Steps 1004, 1005, 1006, and 1007 are similar to the steps 614, 616, 618, and 620, respectively. In step 1004, the stent 104 and the mandrel 148 are concurrently rotated about and oscillated along the axis 174 defined by the mandrel 148. In step 1005, a syringe pump (such as the syringe pump 106) is fitted with a syringe (such as the syringe 112) containing an amount of an electrospinning material (such as the electrospinning material 102). In step 1006, the syringe 112 is connected to a spinneret (such as the spinneret 126), with the spinneret positioned and oriented so that the spinneret tip 128 is directed toward the exposed portion of the encapsulated stent. In step 1007, a voltage is placed or applied between the spinneret tip 128 and the collector 108.

In step 1008, the electrospinning material 102 is applied to the exposed portion of the encapsulated stent 104 and to at least a portion of the secondary frame 918 and the mandrel 184 to form an extra layer of coating sheet (such as the coating sheet 999). The extra layer of coating sheet covers the exposed portion of the encapsulated stent 104 including the edge of the folded second layer of the excess portion on the outer surface of the stent 104. FIG. 36 shows such a coating sheet 999 formed on the mandrel 148, a portion of the outer surface 932 of the secondary frame 918, and the exposed portion of the encapsulated stent 104. A cone portion 714 of the coating sheet 999 extends from the second end 404 of the stent 104 to the mandrel 148.

In step 1009, the mandrel 148 (along with the encapsulated stent 104 with the extra layer of coating sheet, and the secondary frame 918) is removed from the collector.

In step 1010, similar to step 626, the cone portion 714 and other surplus portions of the extra layer of coating sheet beyond the second end 404 of the stent 104 are removed. The removal of the surplus portions of the coating sheet 999 may be accomplished, for example, by cutting the coating sheet 999 at the second end 404 of the stent 104. The extra layer of coating sheet 999 that covers the exposed portion of the encapsulated stent 104 is left undisturbed, as seen in FIG. 37.

In step 1011, the secondary frame 918 is removed from the mandrel 184.

While various embodiments of the disclosed technology have been described above, it should be understood that they have been presented by way of example only, and not of limitation. Likewise, the various figures may depict an example configuration for the disclosed technology, which is done to aid in understanding the features and functionality that can be included in the disclosed technology. The disclosed technology is not restricted to the illustrated example configurations, but the desired features can be implemented using a variety of alternative configurations.

What is claimed is:

1. A method of applying an electrospun material to an inner surface of a stent, the method comprising:
    coupling a mandrel to a stent body;
        wherein the stent body comprises an inner surface defining a cavity and an outer surface opposing the inner surface, and
        wherein the stent body has a length along an axis defined by the mandrel between a first end of the stent body and a second end of the stent body;
    applying an electrospun material to at least a portion of the stent outer surface and to at least a portion of the mandrel to form a coating sheet;
        wherein a portion of the coating sheet extends from at least one of the first end or second end of the stent to the mandrel; and
    moving one or both of the stent and the mandrel to apply at least some of the portion of the coating sheet onto the inner surface of the stent body.

2. The method of claim 1, wherein coupling the mandrel to the stent body comprises:
    attaching the stent body to a valve holder; and
    threading the valve holder onto the mandrel.

3. The method of claim 2, wherein attaching the stent body to the valve holder comprises suturing the stent body to the valve holder.

4. The method of claim 2, wherein:
    the stent body comprises a plurality of commissure ends;
    the valve holder comprises a plurality of stabilizing legs; and
    attaching the stent body to the valve holder comprises attaching each of the plurality of commissure ends to one of the plurality of stabilizing legs.

5. The method of claim 2, further comprising adhering the valve holder to the mandrel.

6. The method of claim 1, wherein:
    the mandrel comprises a secondary frame portion; and
    the portion of the coating sheet extends from at least one of the first end or second end of the stent to the secondary frame portion of the mandrel.

7. The method of claim 1, further comprising attaching the mandrel to a rotary tool.

8. The method of claim 1, further comprising orienting a spinneret so that the spinneret is directed substantially toward the stent body and substantially perpendicular to the axis defined by the mandrel.

9. The method of claim 8, further comprising placing a voltage between the spinneret and the mandrel.

10. The method of claim 1, wherein applying the electrospun material further comprises concurrently rotating both the mandrel and the stent body about the axis defined by the mandrel and oscillating both the mandrel and the stent body along the axis defined by the mandrel.

11. The method of claim 1, wherein moving one or both of the stent and the mandrel produces an inverted portion of the coating sheet extending inside the cavity of the stent.

12. The method of claim 1, wherein:
the portion of the coating sheet comprises an excess portion that extends axially beyond the second end of the stent body such that that the excess portion is not applied onto the inner surface of the stent body; and
the method further comprises folding the excess portion back to apply at least some of the excess portion onto the outer surface of the stent body.

13. The method of claim 1, further comprising:
providing a filter covering a portion of the stent; and
applying an electrospun material to at least a portion of the outer surface of the stent that is not covered by the filter.

14. A method of applying an electrospun material to an inner surface of a stent, the method comprising:
coupling a mandrel to a stent body;
wherein the stent body comprises an inner surface defining a cavity and an outer surface opposing the inner surface, and
wherein the stent body has a length along an axis defined by the mandrel between a first end of the stent body and a second end of the stent body; and
coupling a secondary frame to the mandrel;
applying an electrospun material to at least a portion of the stent outer surface and to at least a portion of the secondary frame to form a coating sheet;
wherein a portion of the coating sheet extends from at least one of the first end or second end of the stent to the secondary frame; and
moving one or both of the stent and the secondary frame to apply at least some of the portion of the coating sheet onto the inner surface of the stent body.

15. The method of claim 14, wherein:
the stent has a stent diameter;
the secondary frame has a secondary frame diameter; and
the stent diameter is greater than the secondary frame diameter.

16. The method of claim 14, further comprising positioning the stent body so that the stent body is between the secondary frame and the valve holder.

17. The method of claim 14, further comprising positioning the stent body so that the secondary frame extends within the cavity of the stent body.

18. The method of claim 14, wherein applying the electrospun material further comprises concurrently rotating both the stent body and the secondary frame about the axis defined by the mandrel and oscillating both the stent body and the secondary frame along the axis defined by the mandrel.

19. The method of claim 14, wherein moving one or both of the stent and the secondary frame produces an inverted portion of the coating sheet extending inside the cavity of the stent.

20. The method of claim 14, wherein:
the portion of the coating sheet comprises an excess portion that extends axially beyond the second end of the stent body such that that the excess portion is not applied onto the inner surface of the stent body; and
the method further comprises folding the excess portion back to apply at least some of the excess portion onto the outer surface of the stent body.

21. A method of applying an electrospun material to an inner surface of a stent, the method comprising:
providing a stent defining an axis and having
an inner surface,
an outer surface,
a first end,
a second end, and
a central cavity;
extending a mandrel axially within the central cavity of the stent;
rotating the stent and the mandrel along the axis;
applying an electrospun material to at least a portion of the outer surface of the stent, and to at least a portion of the mandrel, while the stent and the mandrel are rotating along the axis, so that a sheet of the electrospun material is formed, tapering from at least one of the first end or the second end of the stent to the mandrel;
moving either or both of the stent and the mandrel along the axis so that at least a portion of the sheet of the electrospun material is inverted within the central cavity of the stent; and
covering at least a portion of the inner surface of the stent with the portion of the sheet of the electrospun material.

* * * * *